United States Patent [19]

Powers et al.

[11] Patent Number: 5,324,648

[45] Date of Patent: * Jun. 28, 1994

[54] SUBSTITUTED ISOCOUMARINS AS SERINE PROTEASE INHIBITORS AND ANTI-INFLAMMATORY AGENTS

[75] Inventors: James C. Powers, Atlanta; Chih-Min Kam, Roswell, both of Ga.; Josef Oleksyszyn, Westminster, Colo.; J. A. Glinski, New Fairfield, Conn.; M. A. Hernandez, Norcross, Ga.

[73] Assignee: Georgia Tech Research Corporation, Atlanta, Ga.

[*] Notice: The portion of the term of this patent subsequent to Jun. 24, 2003 has been disclaimed.

[21] Appl. No.: 900,515

[22] Filed: Jun. 17, 1992

Related U.S. Application Data

[63] Continuation of Ser. No. 516,289, Apr. 30, 1990, abandoned, which is a continuation-in-part of Ser. No. 215,994, Jul. 7, 1988, abandoned, and Ser. No. 374,980, Jul. 3, 1989, Pat. No. 4,954,519.

[51] Int. Cl.$^5$ ............ C12N 9/99; C12N 9/48; C12N 9/50; C12N 9/66
[52] U.S. Cl. ............ 435/184; 435/212; 435/213; 435/214; 435/215; 435/217; 435/218; 435/219
[58] Field of Search ............ 435/184, 212, 213, 214, 435/215, 217, 218, 219; 514/457, 456

[56] References Cited

U.S. PATENT DOCUMENTS

| | | | |
|---|---|---|---|
| 4,596,822 | 6/1986 | Powers et al. | 514/459 |
| 4,665,670 | 5/1987 | Krantz et al. | 514/232 |
| 4,745,116 | 5/1988 | Krantz et al. | 514/230.5 |
| 5,109,018 | 4/1992 | Powers et al. | 514/457 |

OTHER PUBLICATIONS

Hemmi et al., Biochemistry 24:1841–1848 (1985).
Kam et al., J. Am. Chem. Soc. 109:5044–5045 (1987).
Harper et al., J. Am. Chem. Soc. 106:7618–7619 (1984).
Harper et al., Biochemistry 24:7200–7213 (1985).
Hudig et al., BBRC 149:882–888 (1987).
Kam et al., Biochemistry 27:2547–2557 (1988).

*Primary Examiner*—Douglas W. Robinson
*Assistant Examiner*—S. Saucier
*Attorney, Agent, or Firm*—Deveau, Colton & Marquis

[57] ABSTRACT

Substituted isocoumarins, their use in inhibiting serine proteases with trypsin-like, chymotrypsin-like and elastase-like specificity and their roles as anti-inflammatory agents.

5 Claims, No Drawings

SUBSTITUTED ISOCOUMARINS AS SERINE PROTEASE INHIBITORS AND ANTI-INFLAMMATORY AGENTS

This is a continuation of copending application Ser. No. 07/516,289 filed on Apr. 30, 1990 now abandoned, which is a continuation-in-part of application Ser. No. 374,980, filed on Jul. 3, 1989 now U.S. Pat. No. 4,954,519 and application Ser. No. 215,994, filed on Jul. 7, 1988, now abandoned.

BACKGROUND OF THE INVENTION

1. Field of the Invention

This invention relates to a novel class of heterocyclic compounds useful for selectively inhibiting trypsin-like enzymes, selectively inhibiting chymotrypsin-like enzymes, selectively inhibiting elastase or for generally inhibiting serine proteases of all classes. This invention also relates to a method of controlling blood coagulation, complement activation, fibrinolysis, tumor invasiveness and treating inflammation, blistering, viral infection in patients using the novel compounds of the present invention. We have found that isocoumarins substituted with basic groups are potent inhibitors of blood coagulation enzymes, tryptases, plasmin, complement proteins, and cytotoxic lymphocyte granzymes and isocoumarins substituted with hydrophobic groups are potent inhibitors of chymases and elastases, therefore they are useful as anticoagulants, anti-inflammatory and anti-tumor agents.

2. Description of the Related Art

Serine proteases play critical roles in several physiological processes such as digestion, blood coagulation, complement activation, fibrinolysis, viral infection, fertilization, and reproduction. Serine proteases are not only a physiological necessity, but also a potential hazard if they are not controlled. Blood coagulation serine proteases are responsible for vascular clotting, cerebral infarction, and coronary infarction. Plasmin and plasminogen activator are involved in tumor invasiveness, tissue remodeling, blistering, and clot dissociation. Uncontrolled proteolysis by elastases may cause pancreatitis, emphysema, rheumatoid arthritis, bronchial inflammation and adult respiratory distress syndrome. It has been suggested that a new trypsin-like cellular enzyme is involved in the infection of human immunodeficiency virus type 1 (HIV-1; Hattori et al., FEBS Letters 248, pp 48-52 (1989)), which is a causative agent of acquired immunodeficiency syndrome (AIDS). Accordingly, specific and selective inhibitors of these proteases should be potent anticoagulants, anti-inflammatory agents, anti-tumor agents and anti-viral agents useful in the treatment of protease-related diseases (Powers and Harper, in Proteinase Inhibitors, Barrett and Salvesen, eds., Elsevier, 1986, pp 55–152, incorporated herein by reference). In vitro proteolysis by trypsin, chymotrypsin or the elastase family is a serious problem in the production, purification, isolation, transport or storage of peptides and proteins.

Anticoagulants and antithrombotic drugs are used in a variety of thrombotic disorders. The 1986 Physician's Desk Reference lists three anticoagulant drugs (heparin, protamine sulfate and warfarin), one antiplatelet drug (aspirin) and several thrombolytic agents. Heparin and warfarin are commonly used clinically for prevention and treatment of venous thrombosis and pulmonary embolism. Heparin inhibits the blood coagulation activity by accelerating the binding of natural plasma protease inhibitor antithrombin III with coagulation factors, and warfarin acts as a vitamin K antagonist and inhibits the synthesis of coagulation factors. None of the anticoagulant drugs, antithrombotic drugs, fibrinolytic agents and antiplatelet drugs are highly effective in all clinical situations and many induce side reactions (Von Kaulla in Burger's Medicinal Chemistry, Part II, Wolff ed, 1979, pp 1081–1132, incorporated herein by reference). Coagulation disorders such as disseminated intravascular coagulation, bleeding complications of medical and surgical procedures and bleeding complications of systemic illness are still difficult to manage (Ingram, Brozovic and Slater in Bleeding Disorders, Blackwell Scientific Publications, 1982, pp 1–413). In the treatment of patients with coagulation problems, anticoagulant or antithrombotic agents of diverse mechanisms are urgently sought in order to provide better medical care.

Anti-inflammatory agents are used to treat elastase-associated inflammation including rheumatoid arthritis and emphysema. Although the naturally occurring protease inhibitor, $\alpha$1-protease inhibitor ($\alpha$1-PI) has been used to treat patients with emphysema, this inhibitor is not widely used clinically due to the high dosage needed for the treatment and difficulty of producing large quantities. Therefore small molecular weight elastase inhibitors are needed for therapy.

SUMMARY OF THE INVENTION

It is an object of this invention to find a novel group of specific inhibitors for trypsin, elastase, chymotrypsin and other serine proteases of similar substrate specificity and for serine proteases in general. Inhibitors are compounds that reduce or eliminate the catalytic activity of the enzyme. Trypsin and trypsin-like enzymes normally cleave peptide bonds in proteins and peptides where the amino acid residue on the carbonyl side of the split bond ($P_1$ residue) is Lys or Arg. Elastase and elastase-like enzymes, on the other hand, cleave peptide bonds where the $P_1$ amino acid is Ala, Val, Ser, Leu and other similar amino acids. Chymotrypsin and chymotrypsin-like enzymes hydrolyze peptide bonds where $P_1$ amino acid is Trp, Tyr, Phe, Met, Leu or other amino acid residues which contain aromatic or large alkyl side chains. All of the above enzymes have extensive secondary specificity and recognize amino acid residues removed from the $P_1$ residue.

It is an object of this invention to discover new protease inhibitors, especially blood coagulation enzyme inhibitors, which can act as anticoagulants in vitro and in vivo. Such inhibitors could be used in prevention of thrombosis during periods of stasis and/or endothelial damage in segments of vasculature. They could also be used in an adjunct to fibrinolytic therapy to prevent acute coronary or peripheral artery reclosure. The inhibitors of this invention would be useful as the sole method of maintaining anticoagulation in extracorporeal blood circuits such as the kidney hemodialysis, and heart lung bypass. Such inhibitors could also be used as alternate anticoagulants when conventional anticoagulation with heparin or coumarin fail or is contraindicated. The inhibitors of this invention would also be useful in the therapy for disseminated intravascular coagulation syndromes (DIC). They could also be used in prophylaxis against thrombosis in high risk situations involving myocardium (e.g. unstable angina).

It is another object of this invention to discover new protease inhibitors, especially elastase inhibitors, tryptase inhibitors, chymase inhibitors and plasmin inhibitors. These inhibitors are useful for controlling tissue damage and various inflammatory conditions mediated by proteases particularly elastases. The inhibitors of this invention would be useful for treating diseases related to plasmin such as tumor invasiveness and blistering. The inhibitors of this invention would also be useful for controlling hormone processing by serine proteases and for treating diseases related to tryptases and chymases such as inflammation and skin blistering. The inhibitors of this invention are useful for treating diseases related to tryptases and caused by viral infection such as AIDS.

It is a further object of this invention to find a novel group of specific inhibitors useful in vitro for inhibiting trypsin, elastase, chymotrypsin and other serine proteases of similar specificity and for inhibiting serine proteases in general. Such inhibitors could be used to identify new proteolytic enzymes encountered in research. They could also be used in research and industrially to prevent undesired proteolysis that occurs during the production, isolation, purification, transport and storage of valuable peptides and proteins. Such proteolysis often destroys or alters the activity and/or function of the peptides and proteins. Uses would include the addition of the inhibitors to antibodies, enzymes, plasma proteins, tissue extracts or other proteins and peptides which are widely sold for use in clinical analyses, biomedical research, and for many other reasons. For some uses a specific inhibitor would be desirable, while in other cases, an inhibitor with general specificity would be preferred.

DETAILED DESCRIPTION OF THE INVENTION

Isocoumarins with cationic substituents have been found to be excellent inhibitors of several serine proteases including bovine trypsin, bovine thrombin, human thrombin, bovine factor Xa, human factor Xa, human factor XIa, human factor XIIa, human factor VIIa, porcine pancreatic kallikrein, human plasma kallikrein, human plasma plasmin, human tissue plasminogen activator, Complement proteins C1r̄, C1s̄, D, B, and C2), sheep lymph tryptase, human lung tryptase, rat skin tryptase, mouse cytotoxic lymphocyte granzyme A, human cytotoxic lymphocyte granzyme A, human cytotoxic lymphocyte Q31 tryptase. Isocoumarins with hydrophobic substituents have been found to be excellent inhibitors of several serine proteases including human leukocyte elastase, porcine pancreatic elastase, bovine chymotrypsin, human leukocyte cathepsin G, rat mast cell protease II, human skin chymase, and human lung chymase. These compounds inhibit the serine proteases by reaction with the active site serine to form an acyl enzyme, which in some cases may further react with another active site nucleophile to form an additional covalent bond. These structures may be used in vivo to treat diseases resulting from uncontrolled blood coagulation or diseases caused by uncontrolled proteolysis by elastase, chymotrypsin, trypsin and related serine proteases. These inhibitors may be used in vitro to prevent proteolysis which occurs in the process of production, isolation, purification, storage or transport of peptides and proteins. The novel substituted isocoumarin and related heterocyclic compounds have the following structural formula:

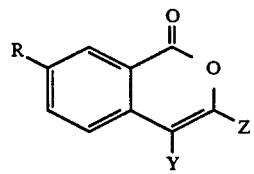

(I)

or a pharmaceutically acceptable salt, wherein

R is selected from the group consisting of H, OH, $NH_2$, $NO_2$, halogen, $C_{1-6}$ alkoxy, $C_{1-6}$ fluorinated alkoxy, $C_{1-6}$ alkyl, O=C=N—, S=C=N—, AA—NH—, AA—AA—NH—, AA—O—, AA—AA—O—, M—NH—, M—AA—NH—, M—AA—AA—NH—, M—O—, M—AA—O—, M—AA—AA—O—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, wherein M represents $NH_2$—CO—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—, wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, wherein K represents halogen, COOH, OH, CN, $NO_2$, $NH_2$, $C_{1-6}$ alkoxy, $C_{1-6}$ alkylamine, $C_{1-6}$ dialkylamine, or $C_{1-6}$ alkyl-O—CO—, or $C_{1-6}$ alkyl-O—CO—NH—, Z is selected from the group consisting of $C_{1-6}$ alkoxy with an amino group attached to the alkoxy group, $C_{1-6}$ alkoxy with an isothiureido group attached to the alkoxy group, $C_{1-6}$ alkoxy with a guanidino group attached to the alkoxy group, $C_{1-6}$ alkoxy with an amidino group attached to the alkoxy group, $C_{1-6}$ alkyl with an amino group attached to the alkyl group, $C_{1-6}$ alkyl with an isothiureido group attached to the alkyl group, $C_{1-6}$ alkyl with an guanidino group attached to the alkyl group, $C_{1-6}$ alkyl with an amidino group attached to the alkyl group, and Y is selected from the group consisting of H, halogen, trifluoromethyl, methyl, OH and methoxy.

Alternately the novel isocoumarin and related heterocyclic compounds are represented by structure (I) where, wherein R is selected from the group consisting of O=C=N—, S=C=N—, M—NH—, M—AA—NH—, M—AA—AA—NH—, M—O—, M—AA—O, M—AA—AA—O—, wherein M represents $NH_2$—CO—, $NH_2$—CS—, $NH_2$—$SO_2$—, X—NH—CO—, X—NH—CS—, X—N-

H—SO$_2$—, X—CS—, X—O—CO—, X—O—CS—, benzoyl with J substituent attached to benzoyl group, phenylsulfonyl with J substituent attached to phenylsulfonyl group, C$_{1-6}$ alkylsulfonyl with K substituent attached to C$_{1-6}$ alkylsulfonyl group, C$_{2-6}$ alkanoyl with phenyl group attached to C$_{2-6}$ alkanoyl group, or C$_{2-6}$ alkanoyl with phenyl group substituted with J attached to C$_{2-6}$ alkanoyl group, wherein X represents C$_{1-6}$ alkyl, C$_{1-6}$ fluoroalkyl, C$_{1-6}$ alkyl substituted with K, C$_{1-6}$ fluoroalkyl substituted with K, 9-fluorenylmethyl, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, C$_{1-6}$ alkyl with two attached phenyl groups, C$_{1-6}$ alkyl with an attached phenyl group substituted with J, or C$_{1-6}$ alkyl with two attached phenyl groups substituted with J, wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl-O—CO—, C$_{1-6}$ alkyl-O—CO—NH—, or C$_{1-6}$ alkyl-S—, wherein K represents halogen, COOH, OH, CN, NO$_2$, NH$_2$, C$_{1-6}$ alkylamine, C$_{1-6}$ dialkylamine, C$_{1-6}$ alkyl-O—, C$_{1-6}$ alkyl-O—CO—NH, C$_{1-6}$ alkyl-S—, or tosylamino, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, Z is C$_{1-6}$ alkyl, C$_{1-6}$ alkoxy, C$_{1-6}$ alkyl with a phenyl group attached to the C$_{1-6}$ alkoxy, C$_{1-6}$ alkoxy with a phenyl group attached to the C$_{1-6}$ alkoxy, and Y is selected from the group consisting of H, halogen, trifluoromethyl, methyl, OH and methoxy.

Alternately the novel isocoumarin and related heterocyclic compounds are represented by structure (I) where, R is selected from the group consisting of OH, NH$_2$, NO$_2$, O=C=N—, S=C=N—, AA—NH—, AA—AA—NH, AA—O—, AA—AA—O—, M—NH—, M—AA—NH—, M—AA—AA—NH—, M—O—, M—AA—O, M—AA—AA—O—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, wherein M represents NH$_2$—CO—, NH$_2$—CS—, NH$_2$SO$_2$—, X—NH—CO—, X—NH—CS—, X—NH—SO$_2$—, X—CO—, X—CS—, X—SO$_2$—, X—O—CO—, or X—O—CS—, wherein X represents C$_{1-6}$ alkyl, C$_{1-6}$ fluoroalkyl, C$_{1-6}$ alkyl substituted with K, C$_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, C$_{1-6}$ alkyl with two attached phenyl groups, C$_{1-6}$ alkyl with an attached phenyl group substituted with J, or C$_{1-6}$ alkyl with two attached phenyl groups substituted with J, wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl-O—CO—, C$_{1-6}$ alkyl-O—CO—NH—, or C$_{1-6}$ alkyl-S—, wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl-O—CO—, or C$_{1-6}$ alkyl-O—CO—NH—, C$_{1-6}$ alkyl-S—, or tosylamino, Z is selected from the group consisting of C$_{1-6}$ alkoxy with a halogen attached to the alkoxy group, C$_{1-6}$ alkyl with a halogen attached to the alkyl group, C$_{1-6}$ alkoxy with an attached C$_{1-6}$ alkoxy group substituted with Q, wherein Q represents H, or C$_{1-6}$ alkoxy, and Y is selected from the group consisting of H, halogen, trifluoromethyl, methyl, OH and methoxy.

Alternately the novel isocoumarin and related heterocyclic compounds are represented by structure (I) where, R is selected from the group consisting of —NH—C(=NH)NH$_2$, —C(=NH)NH$_2$, C$_{1-6}$ alkyl with an amino group attached to the C$_{1-6}$ alkyl, C$_{1-6}$ alkyl with an isothiureido group of the formula —S—C(=NH)NH$_2$ attached to the alkyl group, Z is selected from the group consisting of H, halogen, C$_{1-6}$ alkyl, C$_{1-6}$ fluorinated alkyl, C$_{1-6}$ alkyl substituted with K, C$_{1-6}$ fluorinated alkyl substituted with K, C$_{1-6}$ alkoxy, C$_{1-6}$ fluorinated alkoxy, C$_{1-6}$ alkoxy substituted with K, C$_{1-6}$ fluorinated alkoxy substituted with K, C$_{1-6}$ alkyl with a phenyl group attached to the alkyl group, C$_{1-6}$ alkoxy with a phenyl group attached to the alkoxy group, C$_{1-6}$ alkyl with an attached phenyl group substituted with J, C$_{1-6}$ alkyl with an attached phenyl group disubstituted with J, C$_{1-6}$ alkoxy with an attached phenyl group substituted with J, C$_{1-6}$ alkoxy with an attached phenyl group disubstituted with J, wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl-O—CO—, C$_{1-6}$ alkyl-O—CO—NH—, or C$_{1-6}$ alkyl-S—, wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl-O—CO—, or C$_{1-6}$ alkyl-O—CO—NH—, C$_{1-6}$ alkyl-S-, or tosylamino, and Y is selected from the group consisting of H, halogen, trifluoromethyl, methyl, OH, and methoxy.

Alternatively the novel isocoumarin and related heterocyclic compounds are represented by structure (I) where, R is selected from the group consisting of —NH—C(=NH)NH$_2$, —C(=NH)NH$_2$, C$_{1-6}$ alkyl with an amino group attached to the C$_{1-6}$ alkyl, C$_{1-6}$ alkyl with an isothiureido group attached to the C$_{1-6}$ alkyl, Z is selected from the group consisting of C$_{1-6}$ alkoxy with an amino group attached to the alkoxy group, C$_{1-6}$ alkoxy with an isothiureido group attached to the alkoxy group, C$_{1-6}$ alkoxy with a guanidino group attached to the alkoxy group, C$_{1-6}$ alkoxy with an amidino group attached to the alkoxy group, C$_{1-6}$ alkyl with an amino group attached to the alkyl group, C$_{1-6}$ alkyl with an isothiureido group attached to the alkyl group, C$_{1-6}$ alkyl with a guanidino group attached to the alkyl group, C$_{1-6}$ alkyl with an amidino group attached to the alkyl group, and Y is selected from the group consisting of H, halogen, trifluoromethyl, methyl, OH and methoxy.

Alternately the novel isocoumarin and related heterocyclic compounds are represented by structure (I) where, R is biotin-spacer-T, wherein T represents —NH—, —O—, or —S—, Spacer represents —[NH—(CH$_2$)$_n$—CO]$_n$—, —[NH—(CH$_2$)$_n$—NH—CO]$_n$—, —(NH—C$_6$H$_4$—CO)$_n$—, —(NH—C$_6$H$_4$—NH—CO)$_n$—, —NH—(CH$_2$)$_n$—CO—NH—(CH$_2$)$_n$—NH—CO—, —NH—(CH$_2$)$_n$—CO—NH—(CH$_2$)$_3$—NH—(CH$_2$)$_3$—NH—CO—CH$_2$CH$_2$—CO—, or —(AA)$_n$—, where n=1–6, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, Z is selected from the group consisting of H, halogen, C$_{1-6}$ alkyl, C$_{1-6}$ fluorinated alkyl, C$_{1-6}$ alkyl substituted with K, C$_{1-6}$ fluorinated alkyl substituted with K, C$_{1-6}$ alkoxy, C$_{1-6}$ fluorinated alkoxy, C$_{1-6}$ alkoxy substituted with K, C$_{1-6}$ fluorinated alkoxy substituted with K, C$_{1-6}$ alkyl with a phenyl group attached to the alkyl group, C$_{1-6}$ alkoxy with a phenyl group attached to the alkoxy group, C$_{1-6}$ alkyl with an attached phenyl group substituted with J, C$_{1-6}$ alkyl with an attached phenyl group disubstituted with J, C$_{1-6}$ alkoxy with an attached phenyl group substituted with J, C$_{1-6}$ alkoxy with an attached phenyl group disubstituted with J, wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl-O—CO—, C$_{1-6}$ alkyl—O—CO—NH—, or C$_{1-6}$ alkyl-S-, wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl-O—CO—, or C$_{1-6}$ alkyl-O—CO—NH—, C$_{1-6}$ alkyl-S—, or tosylamino, and Y is selected from the group consisting of H, halogen, trifluoromethyl, methyl, OH, and methoxy.

The compounds of Formula (I) can also contain one or more substituents at position B as shown in the following structure:

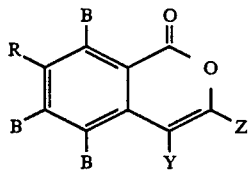

wherein electronegative substituents such as NO$_2$, CN, Cl, COOR, and COOH will increase the reactivity of the isocoumarin, and electropositive substituents such as NH$_2$, OH, alkoxy, thioalkyl, alkyl, alkylamino, and dialkylamino will increase its stability. Neutral substituents could also increase the stability of acyl enzyme and improve the effectiveness of the inhibitors.

Other substituted isocoumarins have been prepared earlier for other purposes (illustrative examples: 3-chloroisocoumarin, Davies and Poole, J. Chem. Soc., pp 1616–1629 (1928); 3-chloro and 3,4-dichloroisocoumarin, Milevskaya, Belinskaya, and Yagupol'skii, Zhur. Org. Khim. 9, pp 2145–2149 (1973); 3-methyl and 4-carboxy-3-methylisocoumarin, Tirodkar and Usgaonkar, Ind. J. Chem. 7, pp 1114–1116 (1969); 7-nitro and 7-aminoisocoumarin, Choksey and Usgaonkar, Ind. J. Chem. 14B, pp 596–598 (1976), the preceding articles are incorporated herein by reference).

A number of other substituted isocoumarins have been prepared recently for inhibition of serine proteases (3-chloroisocoumarin, Harper, Hemmi, and Powers, J. Am. Chem. Soc. 105, pp 6518–6520 (1983); 3,4-dichloroisocoumarin, Harper, Hemmi, and Powers, Biochemistry 24, pp 1831–1841 (1985); 3-alkoxy-7-amino-4-chloroisocoumarin, Harper and Powers, J. Am. Chem. Soc. 106, pp 7618–7619 (1984), Harper and Powers, Biochemistry 24, 7200–7213 (1983); substituted isocoumarins with basic groups such as aminoalkoxy, guanidino or isothiureidoalkoxy, Kam, Fujikawa and Powers, Biochemistry 27, pp 2547–2557 (1988); 7-substituted 3-alkoxy-4-chloroisocoumarins, Powers, Kam, Narasimhan, Oleksyszyn, Hernandez and Ueda, J. Cell Biochem. 39, pp 33–46 (1989), Powers, Oleksyszyn, Narasimhan, Kam, Radhakrishnan and Meyer, Jr. Biochemistry 29, 3108–3118 (1990), the preceding articles are incorporated herein by reference; Powers and Harper, U.S. Pat. No. 4,596,822; Powers and Kam, U.S. Pat. No. 4,845,242 which are also incorporated by reference).

The following compounds are representative of the invention:

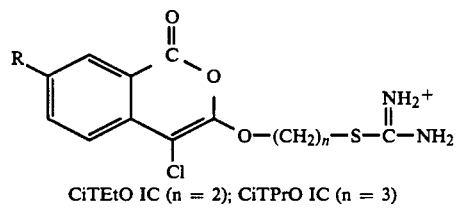

CiTEtO IC (n = 2); CiTPrO IC (n = 3)

7-(benzylcarbamoylamino)-4-chloro-3-(3-isothiureidopropoxy)isocoumarin (PhCH$_2$NHCONH-CiTPrOIC)

7-(phenylcarbamoylamino)-4-chloro-3-(3-isothiureidopropoxy)isocoumarin (PhNHCONH-CiTPrOIC)

7-(acetylamino)-4-chloro-3-(3-isothiureidopropoxy)isocoumarin (CH$_3$CONH-CiTPrOIC)

7-(3-phenylpropionylamino)-4-chloro-3-(3-isothiureidopropoxy)isocoumarin (PhCH$_2$CH$_2$CONH-CiTPrOIC)

7-(phenylacetylamino)-4-chloro-3-(3-isothiureidopropoxy)isocoumarin (PhCH$_2$CONH-CiTPrOIC)

7-(L-phenylalanylamino)-4-chloro-3-(3-isothiureidopropoxy)isocoumarin (L-Phe-NH-CiTPrOIC)

7-(N-t-butyloxycarbonyl-L-phenylalanylamino)-4-chloro-3-(3-isothiureidopropoxy)isocoumarin (Boc-L-Phe-NH-CiTPrOIC)

7-(D-phenylalanylamino)-4-chloro-3-(3-isothiureidopropoxy)isocoumarin (D-Phe-NH-CiTPrOIC)

7-(N-t-butyloxycarbonyl-D-phenylalanylamino)-4-chloro-3-(3-isothiureidopropoxy)isocoumarin (Boc-D-Phe-NH-CiTPrOIC)

7-(benzylcarbamoylamino)-4-chloro-3-(2-isothiureidoethoxy)isocoumarin (PhCH$_2$NHCONH-CiTEtOIC)

7-(phenylcarbamoylamino)-4-chloro-3-(2-isothiureidoethoxy)isocoumarin (PhNHCONH-CiTEtOIC)

7-(isopropylcarbamoylamino)-4-chloro-3-(2-isothiureidoethoxy)isocoumarin ((CH$_3$)$_2$CHNHCONH-CiTEtOIC)

7-(phenylacetylamino)-4-chloro-3-(2-isothiureidoethoxy)isocoumarin (PhCH$_2$CONH-CiTEtOIC)
7-(L-phenylalanylamino)-4-chloro-3-(2-isothiureidoethoxy)isocoumarin (L-Phe-NH-CiTEtOIC)
7-(N-t-butyloxycarbonyl-L-phenylalanylamino)-4-chloro-3-(2-isothiureidoethoxy)isocoumarin (Boc-L-Phe-NH-CiTEtOIC)
7-(D-phenylalanylamino)-4-chloro-3-(2-isothiureidoethoxy)isocoumarin (D-Phe-NH-CiTEtOIC)
7-(N-t-butyloxycarbonyl-D-phenylalanylamino)-4-chloro-3-(2-isothiureidoethoxy)isocoumarin (Boc-D-Phe-NH-CiTEtOIC)
7-(N-t-butyloxycarbonyl-L-alanyl-L-alanylamino)-4-chloro-3-(2-isothiureidoethoxy)isocoumarin (Boc-Ala-Ala-NH-CiTEtOIC)
7-(L-alanyl-L-alanylamino)-4-chloro-3-(2-isothiureidoethoxy)isocoumarin (Ala-Ala-NH-CiTEtOIC)
7-(1-naphthylcarbamoylamino)-4-chloro-3-(2-isothiureidoethoxy)isocoumarin (NaphthylNH-CiTEtOIC)
7-((S)-α-methylbenzylcarbamoylamino)-4-chloro-3-(2-isothiureidoethoxy)isocoumarin (S-C$_6$H$_5$(CH$_3$)CHNHCONH-CiTEtOIC)
7-((R)-α-methylbenzylcarbamoylamino)-4-chloro-3-(2-isothiureidoethoxy)isocoumarin (R-C$_6$H$_5$(CH$_3$)CHNHCONH-CiTEtOIC)
7-dansylamino-4-chloro-3-(2-isothiureidoethoxy)isocoumarin (DansylNH-CiTEtOIC)
7-phenylthiocarbamoylamino-4-chloro-3-(2-isothiureidoethoxy)isocoumarin (PhNHCSNH-CiTEtOIC)
7-(m-carboxyphenylthiocarbamoyl)amino-4-chloro-3-(2-isothiureidoethoxy)isocoumarin (m-COOH-PhNHCSNH-CiTEtOIC)
7-(p-carboxyphenylthiocarbamoyl)amino-4-chloro-3-(2-isothiureidoethoxy)isocoumarin (p-COOH-PhNHCSNH-CiTEtOIC)
7-(L-alanylamino)-4-chloro-3-methoxyisocoumarin
7-(glycylamino)-4-chloro-3-methoxyisocoumarin
7-isocyanato-4-chloro-3-methoxyisocoumarin
7-ethoxycarbonylamino-4-chloro-3-methoxyisocoumarin
7-phenoxycarbonylamino-4-chloro-3-methoxyisocoumarin
7-benzyloxycarbonylamino-4-chloro-3-methoxyisocoumarin
7-carbamoylamino-4-chloro-3-methoxyisocoumarin
7-methylcarbamoylamino-4-chloro-3-methoxyisocoumarin
7-ethylcarbamoylamino-4-chloro-3-methoxyisocoumarin
7-isopropylcarbamoylamino-4-chloro-3-methoxyisocoumarin
7-t-butylcarbamoylamino-4-chloro-3-methoxyisocoumarin
7-phenylcarbamoylamino-4-chloro-3-methoxyisocoumarin
7-(N-benzyl-N-phenylethylcarbamoyl)amino-4-chloro-3-methoxyisocoumarin
7-heptafluorobutyroylamino-4-chloro-3-methoxyisocoumarin
7-(9-fluorenylmethoxycarbonyl)amino-4-chloro-3-methoxyisocoumarin
7-(N-tosyl-α-phenylglycyl)amino-4-chloro-3-methoxyisocoumarin
7-(o-phthalyl)amino-4-chloro-3-methoxyisocoumarin
7-(o-methoxyphthalyl)amino-4-chloro-3-methoxyisocoumarin
7-methoxysuccinylamino-4-chloro-3-methoxyisocoumarin
7-methoxyglutarylamino-4-chloro-3-methoxyisocoumarin
7-(3-phenylglutaryl)amino-4-chloro-3-methoxyisocoumarin
7-(m-methoxycarbonylaminobenzoyl)amino-4-chloro-3-methoxyisocoumarin
7-ethoxycarbonylamino-4-chloro-3-ethoxyisocoumarin
7-ethylthiocarbamoylamino-4-chloro-3-ethoxyisocoumarin
7-phenylthiocarbamoylamino-4-chloro-3-ethoxyisocoumarin
7-dihydrocinnamoylamino-4-chloro-3-propyloxyisocoumarin
7-ethoxycarbonylamino-4-chloro-3-propyloxyisocoumarin
7-ethylcarbamoylamino-4-chloro-3-propyloxyisocoumarin
7-phenylcarbamoylamino-4-chloro-3-propyloxyisocoumarin
7-phenylthiocarbamoylamino-4-chloro-3-propyloxyisocoumarin
7-benzylthiocarbamoylamino-4-chloro-3-propyloxyisocoumarin
7-(m-nitrobenzoyl)amino-4-chloro-3-propyloxyisocoumarin
7-[(2-thiomethyl)acetyl]amino-4-chloro-3-propyloxyisocoumarin
7-(N-t-butyloxycarbonyl-valyl)amino-4-chloro-3-propyloxyisocoumarin
7-nitro-4-chloro-3-(2-bromoethoxy)isocoumarin
7-amino-4-chloro-3-(2-bromoethoxy)isocoumarin
7-t-butylcarbamoylamino-4-chloro-3-(2-bromoethoxy)isocoumarin
7-isopropylcarbamoylamino-4-chloro-3-(2-bromoethoxy)isocoumarin
7-phenylcarbamoylamino-4-chloro-3-(2-bromoethoxy)isocoumarin
7-benzylcarbamoylamino-4-chloro-3-(2-bromoethoxy)isocoumarin
7-(R-α-methylbenzyl)carbamoylamino-4-chloro-3-(2-bromoethoxy)isocoumarin
7-(S-α-methylbenzyl)carbamoylamino-4-chloro-3-(2-bromoethoxy)isocoumarin
7-naphthylcarbamoylamino-4-chloro-3-(2-bromoethoxy)isocoumarin
7-t-butylacetylamino-4-chloro-3-(2-bromoethoxy)isocoumarin
7-phenylacetylamino-4-chloro-3-(2-bromoethoxy)isocoumarin
7-(N-t-butyloxycarbonyl-D-phenylalanyl)amino-4-chloro-3-(2-bromoethoxy)isocoumarin
7-(N-t-butyloxycarbonyl-L-phenylalanyl)amino-4-chloro-3-(2-bromoethoxy)isocoumarin
7-(N-t-butyloxycarbonyl-L-alanylalanyl)amino-4-chloro-3-(2-bromoethoxy)isocoumarin
7-dansylamino-4-chloro-3-(2-bromoethoxy)isocoumarin
7-phenylthiocarbamoylamino-4-chloro-3-(2-bromoethoxy)isocoumarin
7-(m-carboxyphenyl)thiocarbamoylamino-4-chloro-3-(2-bromoethoxy)isocoumarin
7-(p-carboxyphenyl)thiocarbamoylamino-4-chloro-3-(2-bromoethoxy)isocoumarin
7-nitro-4-chloro-3-(3-bromopropoxy)isocoumarin
7-amino-4-chloro-3-(3-bromopropoxy)isocoumarin
7-phenylcarbamoylamino-4-chloro-3-(3-bromopropoxy)isocoumarin 7-benzylcarbamoylamino-4-chloro-3-(3-bromopropoxy)isocoumarin
7-acetylamino-4-chloro-3-(3-bromopropoxy)isocoumarin
7-phenylacetylamino-4-chloro-3-(3-bromopropoxy)isocoumarin
7-dihydrocinnamoylamino-4-chloro-3-(3-bromopropoxy)isocoumarin
7-(N-t-butyloxycarbonyl-D-phenylalanyl)amino-4-chloro-3-(3-bromopropoxy)isocoumarin
7-(N-t-butyloxycarbonyl-L-phenylalanyl)amino-4-chloro-3-(3-bromopropoxy)isocoumarin
7-nitro-4-chloro-3-(2-bromoisopropoxy)isocoumarin
7-amino-4-chloro-3-(2-bromoisopropoxy)isocoumarin
7-amino-4-chloro-3-(2-methoxy)ethoxyisocoumarin
7-amino-4-chloro-3-[2-(2-methoxyethoxy)etoxy]isocoumarin
3-(3-aminopropoxy)isocoumarin
3-(3-aminopropoxy)-4-chloroisocoumarin
3-(2-isothiureidoethoxy)-4-chloroisocoumarin
3-(3-isothiureidopropoxy)-4-chloroisocoumarin
7-amino-4-chloro-3-(2-isothiureidoethoxy)isocoumarin
7-amino-4-chloro-3-(3-isothiureidopropoxy)isocoumarin
7-guanidino-3-methoxyisocoumarin
7-guanidino-4-chloro-3-methoxyisocoumarin
7-guanidino-3-ethoxyisocoumarin
7-guanidino-4-chloro-3-ethoxyisocoumarin
7-guanidino-3-(2-phenylethoxy)isocoumarin
7-guanidino-4-chloro-3-(2-phenylethoxy)isocoumarin
7-biotinylamino-4-chloro-3-propyloxyisocoumarin
7-biotinylamino-4-chloro-3-(2-phenylethoxy)isocoumarin
7-(6-biotinylaminocaproyl)amino-4-chloro-3-ethoxyisocoumarin
7-(6-biotinylaminocaproyl)amino-4-chloro-3-propyloxyisocoumarin
7-(6-biotinylaminocaproyl)amino-4-chloro-3-(2-phenylethoxy)isocoumarin It has been found that compounds of Formula (I) have anticoagulant activity as shown in Table I, VIII by effective inhibition of the proteolytic function of blood coagulation enzymes in Hepes buffer. Compounds of Formula (I) also have anticoagulant effect in vitro as shown in Table XIX by prolongation of the prothrombin time (PT) and activated partial thromboplastin time (APTT) in human, rabbit and pig plasma. Compounds of Formula (I) are effective in the treatment of organ rejection and autoimmune diseases as shown in Table II by the effective inhibition of the proteolytic function of complement proteins. Compounds of Formula (I) are effective in the detection, prevention and inhibition of adult and infantile respiratory distress syndrome (a consequence of acute lung injuries) as shown in Table III, and IX by the effective inhibition of the proteolytic function of sheep lung lymph tryptase and human lung tryptase. Sheep lung lymph tryptase is utilized as a marker of lung capillary injury, and this is shown in the articles by Lesser et al., Am. Rev. Respir. Dis. 135, pp 643–650 (1987) and by Orlowski et al., Arch. Biochem. Biophys. 269, pp 125–136 (1989), which are incorporated herein by reference. Compounds of Formula (I) are effective in treating a variety of blistering diseases as shown in Table III, V, and IX by the effective inhibition of proteolytic function of rat skin tryptase, human skin tryptase, rat mast cell protease II and human skin chymase. It has been found that compounds of Formula (I) have anti-tumor activity as shown in Table VI, IX by the effective inhibition of the proteolytic function of human plasma plasmin and human tissue plasminogen activator. Compounds of Formula (I) have anti-viral and anti-tumor activity as shown in Table VII by effective inhibition of proteolytic function of mouse granzyme A, human granzyme A and human Q31 tryptase, which are involved in cell-mediated killing.

It has been found that compounds of Formula (I) have anti-inflammatory activity and can be used to treat and control emphysema, adult respiratory distress syndrome and rheumatoid arthritis as shown in Table IV, X, XI, XII, XIII and XVI by effective inhibition of the proteolytic function of human leukocyte elastase and human cathepsin G. Compounds of Formula (I) are effective in the theraputic use for pancreatitis by inhibiting the proteolytic function of chymotrypsin and pancreatic elastase as shown in Table IV, X, XI, XII, XIII, and XVI. Compounds of Formula (I) are also effective in the prevention of unnecessary proteolysis caused by chymotrypsin and elastase in the process of purification, transport and storage of peptides and proteins as shown in Table IV, X, XI, XII, XIII, and XVI by effective inhibition of chymotrypsin and elastase.

Compounds of Formula (I) with R group consisting of biotinylamino or alkanoylamino with biotinylamino group attached to alkanoylamino, Y group of Cl, and Z group of phenylethoxy group are effective in the inhibition of rat granule chymase as shown in Table XIV. The reactivation of inhibited rat granule chymase by these biotin isocoumarins in the presence of hydroxylamine as shown in Table XV is useful in the purification of these enzymes from rat granules by applying the inhibited granules to the avidin beads, where the biotinylated enzymes form tight complex with avidin and retain on the column. Finally the enzyme can be reactivated and eluted out with hydroxylamine solution.

Inactivation rates of serine proteases by substituted isocoumarins were measured by the incubation method. An aliquot of inhibitor (25 or 50 $\mu$l) in Me$_2$SO was added to a buffered enzyme solution (0.01–2.3 $\mu$M) to initiate the inactivation. Aliquots (50 $\mu$l) were withdrawn at various intervals and the residual enzymatic activity was measured. Me$_2$SO concentration in the reaction mixture was 8–12% (v/v). 0.1 Hepes, 0.01M CaCl$_2$, pH 7.5 buffer was utilized for trypsin and coagulation enzymes. 0.1M Hepes, 0.5M NaCl, pH 7.5 was utilized for other serine proteases. The inhibitor concentrations are shown in all the tables. Peptide thioesters or peptide nitroanilides with appropriate sequence were used as substrates for various serine proteases. All peptide thioester hydrolysis rates were measured with assay mixtures containing 4,4′-dithiodipyridine ($\epsilon_{324}$=19800M$^{-1}$cm$^{-1}$; Grasetti & Murray, Arch. Biochem. Biophys. 119, pp 41–49 (1967)). Peptide 4-nitroanilide nitroanilide hydrolysis was measured at 410 nm ($\epsilon_{410}$=8800M$^{-1}$cm$^{-1}$; Erlanger et al., Arch. Biochem. Biophys. 95, pp 271–278 (1961)). First order inactivation rate constant (k$_{obs}$) were obtained from plots of ln (v$_t$/v$_o$) vs time, and the correlation coefficients were greater than 0.98.

Table I and VIII shows the inactivation rate constants for several trypsin-like serine proteases inhibited by isocoumarins substituted with basic groups. When the isocoumarin structure contains guanidino as R, or amino-alkoxy, isothiureidoalkoxy as Z, and Cl as Y, the compound is generally a good inhibitor for trypsin and blood coagulation enzymes and tryptases. The inactivation of the enzyme is time dependent, and the k$_{obs}$/[I]

values are second order rate constants. In most cases, inactivation of the enzyme occurs at the inhibitor concentration of 5–400 times the enzyme concentration and the first order rate constant $k_{obs}$ is obtained. However, in some cases, the inactivation was too fast to be measured under first order rate condition ([I]>[E], the inactivation rate was measured either in the presence of substrate using the progress curve method as described by Tian and Tsou, Biochemistry 21, pp 1028–1032 (1982) or using the same concentration of enzyme and inhibitor. 7-guanidino-4-chloro-3alkoxyisocoumarins are essentially stoichiometric inactivators of trypsin, thrombin and kallikrein. The inactivation rate of the enzyme depends on the substituents R, Z and Y. The structures with R groups of guanidino, and Y groups of Cl are the best inhibitors for trypsin and all the coagulation enzymes tested. The isocoumarins with R groups of phenylcarbamoylamino or S-methylbenzylcarbamoylamino, Y group of Cl and Z group of isothiureidoethoxy are the best inhibitors toward bovine and human thrombin. The isocoumarin with R group of phenylcarbamoylamino, Y group of Cl and Z group of isothiureidoethoxy is the potent inhibitor for human factor Xa and human factor XIa. The isocoumarin with R group of L-Phe, Y group of Cl and Z group of isothiureidoethoxy is the best inhibitor for human factor XIIa.

Table II shows the inactivation of complement proteins D, B, C2, $\overline{C1r}$, $\overline{C1s}$, and their active fragments C2a, Bb by substituted isocoumarins. The isocouimarin with R groups of amino or hydrogen, Z groups of isothiureidopropoxy, and Y groups of chloro inhibit $\overline{C1r}$ and $\overline{C1s}$ quite potently. 7Guanidino-3-alkoxy-4-chloroisocoumarin inhibit $\overline{C1r}$, $\overline{C1s}$, B and Bb moderately. Although 3-isothiureidoalkoxy-4-chloroisocoumarins inhibit protein B and C2 poorly, while other serine protease inhibitors such as 4-amidinophenylmethane sulfonyl fluoride (APMSF) and 3,4-dichloroisocoumarin do not show any inhibition toward these two enzymes. Table III and IX show the inactivation of sheep lung lymph tryptase, human lung tryptase and rat skin tryptase by substituted isocoumarins. The structure with a R group of guanidino, Z group of alkoxy, and Y group of chloro are good inhibitors for sheep lung lymph tryptase. The isocoumarins with R groups of guanidino or amino, Z groups of alkoxy or isothiureidopropoxy, and Y groups of chloro are potent inhibitors for human lung tryptase and rat skin tryptase. The structures with R groups of substituted amino, Y group of Cl, and Z group of isothiureidoalkoxy are good inhibitors for all three tryptases. Table IV an X show the inactivation rate constants for porcine pancreatic elastase (PPE), human leukocyte elastase (HLE), chymotrypsin and cathepsin G inhibited by substituted isocoumarins. Although the inactivation by the inhibitors was less efficient toward these four enzymes than trypsin-like enzymes, the isocoumarin with R group of guanidino, Y group of Cl, and Z-group of ethoxy is a good inhibitor for PPE, HLE and cathepsin G. The structure with Z-group of 2-phenylethoxy is best at inhibiting chymotrypsin. The structure with R group of phenylcarbamoylamino, Y group of Cl, and Z group of isothiureidoethoxy is a potent inhibitor for HLE. The structure with R group of phenylacetylamino, Y group of Cl, and Z-group of isothiureidopropoxy is best at inhibiting chymotrypsin.

Table V shows the inactivation of rat mast cell protease II, human skin chymase and human lung chymase by substituted isocoumains. The structure with R group of guanidino, Z group of alkoxy, and Y group of chloro were potent inhibitors for rat mast cell protease II and were moderate inhibitors for human skin chymase and human lung chymase. Table VI and IX show the inactivation rate constants for human plasmin and human tissue plasminogen activator by substituted isocoumarins. The structure with R groups of amino or substituted amino, hydrogen or guanidino, Z groups of isothiureidoalkoxy or alkoxy, and Y groups of chloro inhibited both enzymes potently. Table VII shows the inactivation of mouse granzyme A, human granzyme A and human Q31 tryptase by substituted isocoumarins. The isocoumarins with R groups of hydrogen, amino or guanidino, Z groups of isothiureidoalkoxy or alkoxy, and Y groups of chloro were potent inhibitors for all three tryptases.

Table XI also shows the inactivation rate constants of porcine pancreatic elastase (PPE), human leukocyte elastase (HLE) inhibited by substituted isocoumarins. The inactivation by these inhibitors was less efficient toward PPE than HLE. The structures with R group of o-methoxyphthalylamino or phenylcarbamoylamino, Y group of Cl, and Z group of methoxy are best inhibitors for PPE. The structures with R group of Tos-phenylglycylamino or m-methoxycarbonylaminobenzoylamino, Y group of Cl, and Z-group of methoxy are best at inhibiting HLE. The structure with R group of phenylthiocarbamylamino, Y group of Cl, and Z-group of ethoxy is the best inhibitor of PPE. Table XII shows the inhibition of PPE, HLE, chymotrypsin and cathepsin G by substituted isocoumarins. It is unexpected that all the compounds with Y group of Cl and Z group of propoxy are very potent inhibitors of HLE. The structure with R group of phenylcarbamoylamino, or dihydrocinnamoylamino, Y group of Cl, and Z group of propoxy are the best inhibitors of HLE. However they are poor inhibitors of cathepsin G. The structure with R group of ethoxycarbonylamino, Y group of Cl and Z group of propoxy is a good inhibitor for chymotrypsin.

Table XIII shows the inhibition of PPE, HLE, chymotrypsin and cathepsin G by biotin isocoumarin derivatives. The compound with R group of o-biotinylaminocaproylamino, Y group of Cl and Z group of phenylethoxy is a good inhibitor for chymotrysin. The structure with R group of 6-biotinylaminocaproylamino, Y group of Cl and Z group of propoxy or ethoxy are best inhibitors for HLE.

Table XIV shows the inhibition of rat granule chymase and tryptase by biotin isocoumarin derivatives. The structure with R group of 6-biotinylaminocaproylamino, Y group of Cl and Z group of phenylethoxy inactivated chymase instantly with 50% inhibition, and also inhibited tryptase very slowly. Table XV shows the reactivation of inhibited chymotrypsin and rat granule chymase by biotin isocoumarins in buffer and in the presence of hydroxylamine. Inhibited chymotrypsin regained 40–85% of activity and inhibited rat granule chymase regained 30–100% of activity in the presence of hydroxylamine.

Table XVI shows the inhibition of PPE, HLE, chymotrypsin and cathepsin G by isocoumarins substituted with bromoalkoxy group. The structure with R group of R-methylbenzylcarbamylamino, Y group of Cl and Z group of bromoethoxy is the best inhibitor for PPE. It is unexpected that all the compounds with Y group of Cl, Z-group of bromoethoxy are potent inhibitors of HLE, especially the structure with R group of phenylcarbamoylamino is the most potent inhibitor of HLE. The structures with R group of $NO_2$, Y group of Cl, Z group of 2-bromoisopropoxy and R group of phenylacetyl, Y group of Cl, Z-group of bromopropoxy are the best at inhibiting chymotrypsin.

Table XVII shows the half-life for the deacylation of inactivated elastase by 7-substituted isocoumarins. Only the enzyme inactivated by compound with R group of phenylcarbamyl, Y group of Cl, and Z group of methoxy is stable with the half-life more than 48 hrs.

The spontaneous hydrolysis rates of these substituted isocoumarins in Hepes buffer, human and rabbit plasma have been measured and summarized in Table XVIII. The isocoumarins with hydrogen at position 4 are 3–6 times more stable than the compounds with Cl at the same position. 7-Amino-4-chloro-3-(3-isothiureidopropoxy)isocoumarin is fairly stable in both human and rabbit plasma. 7-Guanidino-4-chloro-3-alkoxyisocoumarins are hydrolyzed in human and rabbit plasma with half-lives of 5–8 min. The isocoumarins substituted with phenylcarbamoylamino or benzylcarbamoylamino at the 7-position are more stable than 7-amino-4-chloro-3-(3-isothiureidopropoxy)isocoumarin. The isocoumarins substituted with 7-alkanoylamino group are less stable than the parent 7-amino compound.

Anticoagulants can prolong the clotting time of human plasma and play important roles in the treatment of blood coagulation related diseases such as vascular clotting, cerebral infarction and coronary infarction (Williams et al., Hemotalogy, 3rd ed. McGraw Hill, 1983 and Ingram et al., Bleeding Disorders, 2nd ed. Blackwell Scientific Publications, 1985. These two books are incorporated herein by reference). The presence of certain inhibitors of this invention in pig plasma prolong the prothrombin time and activated partial thromboplastin time quite effectively, therefore these compounds act as anticoagulants in vitro. Currently, there are few anticoagulant and antithrombotic drugs in use clinically, and the inhibitors described in this invention can be used as anticoagulants or antithrombotics in mammals (including man).

Considerable evidence has shown that plasminogen activator, leukocyte elastase and/or related enzymes play a role in tumor cell metastasis (Salo, et al., Int. J. Cancer 30, pp 669–673 (1973); Kao et al., Biochem. Biophys. Res. Comm. 105, pp 383–389 (1982); Powers, J. C. in Modification of Proteins, R. E. Feeney and J. R. Whitaker, eds., Adv. Chem. Ser 198, Amer. Chem. Soc., Wash., D.C. pp 347–367 (1982)), therefore it is suggested that compounds of this invention may have anti-tumor activity.

Pulmonary emphysema is a disease characterized by progressive loss of lung elasticity due to the destruction of lung elastin and alveoli. The destructive changes of lung parentchyma associated with pulmonary emphysema are caused by uncontrolled proteolysis in lung tissues (Janoff, Chest 83 pp 54–58 (1983)). A number of proteases has been shown to induce emphysema in animals (Marco et al., Am. Rev. Respir.Dis. 104, pp 595–598 (1971); Kaplan, J. Lab. Clin. Med. 82, pp 349–356 (1973)), particularly human leukocyte elastase (Janoff, ibid 115, pp 461–478 (1977)). Leukocyte elastase and other mediators of inflammation also appear to play a role in diseases such as mucocutaneous lymph node syndrome (Reiger et al., Eur. J. Pediatr. 140, pp 92–97 (1983) and adult respiratory distress syndrome (Stockley, Clinical Science 64, pp 119–126 (1983); Lee et al., N. Eng. J. Med. 304, pp 192–196 (1981); Rinaldo, ibid 301, 900–909 (1982)).

It is known that in vitro activity of elastase inhibitors correlates with in vivo activity in animal models of emphysema and inflammation (Otterness et al., editors, Advances in Inflammation Research, Vol. 11, Raven Press 1986, and this article is incorporated herein by reference). Prophylactic administration of an inhibitor of elastase significantly diminishes the extent of elastase-induced emphysema (Kleinerman et al., Am. Rev. Resir. Dis. 121, pp 381–387 (1980); Lucey et al., Eur. Respir. J. 2, pp 421–427 (1989)). Thus the novel inhibitors described here should be useful for the treatment of emphysema and inflammation. Elastase inhibitors have been used orally, by injection or by instillation in the lungs in animal studies (Powers, Am. Rev. Respir. Dis., 127, s54–s58 (1983); Powers and Bengali, Am. Rev. Respir. Dis. 134, pp 1097–1100 (1986) and these two articles are incorporated herein by reference). The inhibitors described above can be used by any of these routes.

For treatment of blood coagulation-related diseases, tumor invasiveness, viral infection or inflammation, the compounds of Formula (I) or pharmaceutically acceptable salts may be administered orally, topically or parenterally. The term parenteral as used includes subcutaneous injection, intravenous, intramuscular, intrasternal injection or infusion techniques. The dosage depends primarily on the specific formulation and on the object of the therapy or prophylaxis. The amount of the individual doses as well as the administration is best determined by individually assessing the particular case.

The pharmaceutical compositions containing the active ingredient may be in a form suitable for oral use, for example as tablets, troches, lozenges, aqueous or oily suspensions, dispersible powders or granules, emulsions, hard or soft capsules or syrups or elixirs. Dosage levels of the order to 0.2 mg to 140 mg per kilogram of body weight per day are useful in the treatment of above-indicated conditions (10 mg to 7 gms per patient per day). The amount of active ingredient that may be combined with carrier materials to produce a single dosage form will vary depending upon the host treated and the particular mode of administration.

For injection, the therapeutic amount of the compounds of Formula (I) or their pharmaceutically acceptable salts will normally be in the dosage range from 0.2 to 140 mg/kg of body weight. Administration is made by intravenous, intramuscular or subcutaneous injection. Accordingly, pharmaceutical compositions for parenteral administration will contain in a single dosage form about 10 mg to 7 gms of compounds of Formula (I) per dose. In addition to the active ingredient, these pharmaceutical compositions will usually contain a buffer, e.g. a phosphate buffer which keeps the pH in the range from 3.5 to 7 and also sodium chloride, mannitol or sorbitol for adjusting the isotonic pressure.

A composition for topical application can be formulated as an aqueous solution, lotion, jelly or an oily solution or suspention. A composition in the form of an aqueous solution is obtained by dissolving the compounds of Formula (I) or their pharmaceutically acceptable salts in aqueous buffer solution of pH 4 to 6.5 and if desired, adding a polymeric binder. An oily formulation for topical application is obtained by suspending the compounds of Formula (I) or their pharmaceutically acceptable salts in an oil, optionally with the addition of a swelling agent such as aluminum stearate and/or a surfactant.

To use the above inhibitors in vitro, they are dissolved in an organic solvent such as dimethylsulfoxide or ethanol, and are added to an aqueous solution containing serine proteases. The final concentration of the organic solvent should be less than 25%. The inhibitors may also be added as solids or in suspension. The serine protease inhibitors of this invention would be useful in a variety of experimental procedures where proteolysis is a significant problem. Inclusion of these inhibitors in a radioimmunoassay experiments would result in higher sensitivity. The use of these inhibitors in plasma fractionation procedures would result in higher yields of valuable plasma proteins and would make purification of the proteins easier. The inhibitors disclosed here could be used in cloning experiments utilizing bacterial cultures, yeast and purified cloned product in higher yield.

The following examples are given to illustrate the invention and are not intended to limit it in any manner.

EXAMPLE 1

Preparation of 3-(2-Isothiureidoethoxy)-4-Chloroisocoumarin.

2-Bromoethyl-2-carboxyphenylacetate was prepared from heating 10 g of homophthalic acid (56 mmole) and 21 g of 2-bromoethanol (167 mmole) in 175 ml of benzene with a few drops of conc. sulfuric acid at 90°–110° C. for two hours, yield 64%. TLC shows that it is a pure compound. The cyclization of 2-bromoethyl 2-carboxyphenylacetate with $PCl_5$ was performed by a previous method with modification (Tirodkar, and Usgaonkar, Indian. J. Chem. 7, pp 1114–1116 (1969)). 1.15 g of 2-bromoethyl 2-carboxyphenylacetate was heated with 2.1 g of $PCl_5$ in 90 ml of benzene at 70° C. for 2 hrs. The benzene was removed and the residue triturated with petroleum ether. The crude product was purified by silica gel column chromatography with methylene chloride as an eluent to give 560 mg of 3-(bromoethyl)-4-chloroisocoumarin (yield, 46%). IR and NMR spectra show it was the desired product. 100 mg of 3-bromoethyl-4-chloroisocoumarin (0.3 mmole) was heated with 60 mg of thiourea (0.8 mmole) in 5 ml of THF at 70° C. for 2 days to give a yellow solid, 50 mg (yield, 40%), m.p. 167°–169° C. (dec); one spot on TLC, Rf=0.7 (Butanol:acetic acid:water=6:1:5); NMR spectrum ($d_6$-DMSO), δ 9.1 (2b, 4H), 7.5–8.1 (m, 4H), 4.6 (t, 2H), 3.6 (t, 2H); mass spectrum (FAB+), m/e=299 (M+-Br). Anal. Calc. for $C_{12}H_{12}N_2O_3Br_1Cl_1S_1$: C, 37.96; H, 3.19; N, 7.38. Found: C, 37.81; H, 3.28; N, 7.71.

EXAMPLE 2

Preparation of 7-Guanidino-3-Methoxyisocoumarin

Methyl 2-carboxy-4-nitrophenyl acetate was prepared from 2-carboxy-4-nitrophenylacetate and methanol by the procedure described above. Hydrogenation of this nitro compound gives methyl 4-amino-2-carboxy-phenylacetate (yield 90%). The guanidination of the amino compound with 3,5-dimethylpyrazole-1-carboxamidine nitrate (ADMP) was performed by a standard method described previously (Tsunematsu & Makismi, J. Biochem. 88, pp 1773–1783, (1980)). 2.2 g of amino compound (10 mmole), 1.9 g of triethylamine (19 mmole) and 3.0 g of ADMP (15 mmole) was heated in 20 ml of THF and refluxed for 18 hrs. The white precipitate was filtered and washed with cold methanol to give 1.5 g of methyl 2-carboxy-4-guanidinophenylacetate, (yield 46%). One spot on TLC, Rf=0.6 (Butanol:acetic acid:pyridine:water=4:1:1:2), it shows an orange color when sprayed with Sakaguchi reagent. NMR spectrum ($CF_3COOH$), δ 8.4, 7.7 (b, 4H), 6.6 (b, 4H) 4.4 (s, 2H), 4.1 (s, 3H). Anal. Calc. for $C_{11}H_{13}N_3O_4$. ½ $H_2O$: C, 50.77; H, 5.42; N, 16.15. Found: C, 51.03; H, 5.38; N, 16.19. 0.9 g of methyl 2-carboxy-4-guanidinophenylacetate (3 mmole) was heated with 1.5 g of $PCl_5$ (7.2 mmole) at 70°–80° C. for 2 hrs, white solid precipitated out during the heating. The solid was filtered off and purified by silica gel column chromatography with methylene chloride and methanol (5:1) as an eluent to give 0.5 g of 7-guanidino-3-methoxyisocoumarin (yield 59%). One spot on TLC, Rf=0.7 (Butanol:acetic acid:pyridine:water=4:1:1:2); m.p. 185°–186° C. (dec);, NMR spectrum ($d_6$-DMSO): δ 7.9, 7.6 (b, 3H), 7.7 (b, 4H), 6.1 (s, 1H), 3.9 (s, 3H); mass spectrum (FAB+), m/e=234 (M+-Cl). Anal. Calc. for $C_{11}H_{12}N_3O_3Cl_1$. ½ $H_2O$: C, 47.40; H, 4.67; N, 15.08; Cl, 12.75. Found: C, 47.42; H, 4.74; N, 15.05; Cl, 12.68.

EXAMPLE 3

Preparation of 7-Guanidino-3-Methoxy-4-Chloroisocoumarin.

0.27 g of 7-guanidino-3-methoxyisocoumarin (1 mmole) was chlorinated with 0.15 g of N-chlorosuccinimide (1.1 mmole) in 5 ml DMF at r. t. overnight. The reaction mixture was evaporated to dryness, and purified by silica gel column chromatography which is eluted with methylene chloride and methanol (5:1) to give 0.1 g of 7-guanidino-3-methoxy-4-chloroisocoumarin (yield 34%). One spot on TLC, Rf=0.75 (Butanol:acetic acid:pyridine:water=4:1:1:2); NMR spectrum is similar to 7-guanidino-3-methoxyisocoumarin except no peak at 6.1 ppm; mass spectrum (FAB+), m/e=268 (M+-Cl). Anal. Calc. for $C_{11}H_{11}N_3O_3Cl_2$. ½ $H_2O$: C, 42.17; H, 3.83; N, 13.41; Cl, 22.68. Found: C, 42.65; H, 3.72; N, 13,28; Cl, 22.32.

EXAMPLE 4

Preparation of 7-Amino-4-Chloro-3-(3-Isothiureidopropoxy)isocoumarin.

This compound was synthesized by the same procedure as 3-(3-isothiureidopropoxy)-4-chloroisocoumarin. 3-Bromopropyl 2-carboxy-4-nitrophenylacetate was prepared from 2-carboxy-4-nitrophenylacetate and 3-bromopropanol, yield 60%. Cyclization of the monoester with $PCl_5$ gives 3-bromopropoxy-4-chloro-7-nitroisocoumarin (yield, 60%). Hydrogenation of the nitro compound (0.36 g) in methanol gives 0.12 g of 7-amino-3-bromopropoxy-4-chloroisocoumarin, which is purified by silica gel column chromatography with methylene chloride as an eluent (yield, 36%). This aminoisocoumarin reacts with thiourea in THF to give the final product, which can be crystallized from MeOH-ether (yield, 40%), mp 160°–162° C. (dec); one spot on TLC, Rf=0.6 (Butanol:acetic acid:pyridine water=4:1:1:2); mass spectrum (FAB+), m/e=328 (M+-Br). Anal. Calc. for $C_{13}H_{15}N_3O_3Cl_1Br_1S_1$: C, 38.20; H, 3.70; N, 10.28; Cl, 8.67. Found: C, 38.15; H, 3.73; N, 10.25; Cl, 8.63.

EXAMPLE 5

Preparation of
7-(Alanylamino)-3-Methoxy-4-Chloroisocoumarin
Hydrochloride 7-(N-α-Boc-alanylamino)-3-methoxy-4-chloroisocoumarin was synthesized by reaction of Boc-Ala (1 g, 5.5 mmole) with 1,3-dicyclohexylcarbodiimide (0.57 g, 2.8 mmole) at 0° C. in THF for a few hours (DC Urea was precipitated out), followed by the addition of 7-amino-3-methoxy-4-chloroisocoumarin (0.5 g, 2.2 mmole). The reaction mixture was stirred at r. t. overnight, and DC Urea was then filtered. The reaction mixture was evaporated to dryness, redissolved in $CH_2Cl_2$ and washed with 4% $NaHCO_3$. After evaporating the solvent, the residue was crystallized in THF-Pet Ether to give 0.2 g of Boc-alanylisocoumarin compound, which was identified by NMR spectrum and was shown one spot on TLC. Boc-alanylisocoumarin (0.2 g) was stirred with 25 eq of TFA (1.4 g) in $CH_2Cl_2$ at r.t. for half hour and 1 eq of 3.8N HCl/dioxane was then added. The product was precipitated out when anhydrous ether was added, and was purified by column chromatography ($CH_2Cl_2$: MeOH=7:1), yield 0.1 g, one spot on TLC ($CH_2Cl_2$: MeOH=7:1); NMR ($d_6$-DMSO): δ 7.4–8.4 (m, 3H), 4.0 (s, 3H), 3.1–3.6 (m, 1H), 1.5 (d, 3H).

EXAMPLE 6

Preparation of
7-(Phenylcarbamoylamino)-4-Chloro-3-(2-Isothiureidoethoxy)isocoumarin 7-Amino-3-(2-bromoethoxy)-4-chloroisocoumarin was synthesized as previously described (Powers et al., Biochemistry 29, 3108–3118 (1990)). This compound (0.32 g, 1 mmole) was mixed with phenyl isocyanate (0.12 g, 1 mmole) in 5 ml of THF and the reaction mixture was stirred at r.t. overnight. The product 7-(phenylcarbamoylamino)-4-chloro-3-(2-bromoethoxy)isocoumarin precipitated out, yield 40%, m.p. 215°–217° C., mass spectrum m/e=437.9 (M+). Anal. Calc. for $C_{18}H_{14}N_2O_4ClBr$: C, 49.40; H, 3.22; N, 6.40; Cl, 8.10. Found: C, 49.48; H, 3.25; N, 6.34; Cl, 8.12. The phenylcarbamoylamino compound (0.1 g, 0.23 mmole) was heated with 0.02 g of thiourea (0.26 mmole) in 10 ml of THF at 70° C. overnight. The final product precipitated out, yield 0.04 g, 36%, m.p. 161°–163° C. (dec.), mass spectrum (FAB+) m/e=433 (M-Br). Anal. Calc. for $C_{19}H_{18}N_4O_4ClBrS.0.25$ THF: C, 45.12; H, 3.86; N, 10.53; Cl, 6.67. Found: C, 44.83; H, 3.92; N, 10.12; Cl, 6.41.

7-(Ethylcarbamoylamino)-4-chloro-3-(2-isothiureidoethoxy)isocoumarin, 7-(t-butylcarbamoylamino)-4-chloro-3-(2-isothiureidoethoxy)isocoumarin, 7-(benzylthiocarbamoylamino)-4-chloro-3-(2-isothiureidoethoxy)isocoumarin, 7-(ethylthiocarbamoylamino)-4-chloro-3-(2-isothiureidoethoxy)isocoumarin, 7-(4-fluorobenzyl)thiocarbamoylamino-4-chloro-3-(2-isothiureidoethoxy)isocoumarin, and 7-(2,5-dimethylbenzyl)thiocarbamoylamino-4-chloro-3-(2-isothiureidoethoxy)isocoumarin can be prepared by the same procedure.

EXAMPLE 7

Preparation of
7-(Acetylamino)-4-Chloro-3-(3-Isothiureidopropoxy)isocoumarin

7-Amino-3-(3-bromopropoxy)-4-chloroisocoumarin was synthesized as previously described (Kam et al., 1988). This compound (0.33 g, 1 mmole) was heated with 0.15 g of acetic anhydride (1.5 mmole) in 20 ml of dry THF. After a few minutes, a yellow solid precipitated out. After 3 hrs, the solution was concentrated to 5 ml, and the solid was filtered to give 0.37 g of 7-(acetylamino)-4-chloro-3-(3-bromopropoxy)isocoumarin, m.p. 170°–172° C.; mass spectrum: m/e=375 (M+). The acetylated isocoumarin (0.15 g, 0.4 mmole) was treated with thiourea (0.036 g, 0.47 mmole) to give 0.9 g of the final product, (yield 50%), m.p. 180°–181° C., mass spectrum m/e=370 (M+-Br). Anal. Calc. for $C_{15}H_{17}N_3O_4ClBrS$: C, 39.97; H, 3.80; N, 9.32; Cl 7.87. Found: C, 39.86; H 3.83; N, 9.29; Cl, 7.85.

7-trifluoroacetylamino-4-chloro-3-(3-isothiureidopropoxy)isocoumarin, 7-heptafluorobutyroylamino-4-chloro-3-(3-isothiureidopropoxy)isocoumarin, 7-succinylamino-4-chloro-3-(3-isothiureidopropoxy)isocoumarin, and 7-(o-phthalyl)amino-4-chloro-3-(3-isothiureidopropoxy)isocoumarin can be prepared by the same procedure.

EXAMPLE 8

Preparation of
7-(D-Phenylalanylamino)-4-Chloro-3-(2-Isothiureidoethoxy)isocoumarin Boc-D-Phe (0.33 g, 1.2 mmole) reacted with 1,3-dicyclohexylcarbodiimide (0.13 g, 0.6 mmole) in 10 ml THF at 0° C. for 1 hr to form the symmetric anhydride, and then 7-amino-4-chloro-3-(2-bromoethoxy)isocoumarin (0.2 g, 0.6 mmole) was added. The reaction was stirred at r. t. overnight and the precipitate 7-(Boc-D-Phe-amino)-4-chloro-3-(2-bromoethoxy)isocoumarin was formed (0.29 g, 71%). TLC one spot, m.p. 180°–182° C.; mass spectrum m/e=566 (M+). Anal. Calc. for $C_{25}H_{26}N_2O_6ClBr$: C, 53.07; H, 4.63; N, 4.95; Cl 6.27. Found: C, 53.25; H, 4.66; N, 4.87; Cl, 6.24. Boc-D-Phe compound (0.2 g, 0.35 mmole) was reacted with thiourea (0.027 g, 0.35 mmole) in the same manner to give 7-(Boc-D-phenylalanylamino)-4-chloro-3-(2-isothiureidoethoxy)isocoumarin (0.14 g), yield 62%, mass spectrum (FAB+) m/e 561 (M+-Br). This compound (0.1 g) was dissolved in 3 ml of THF at 0° C. and then the solvent was evaporated to dryness. The final product precipitated out after addition of ether, one spot TLC ($CH_3CN:H_2O:AcOH=8:1:1$); mass spectrum (FAB+) m/e 462 (M+-Br -$CF_3COO$).

7-Boc-alanylamino-4-chloro-3-(2-isothiureidoethoxy)isocoumarin, 7-benzoylamino-Ala-4-chloro-3-(2-isothiureidoethoxy)isocoumarin, 7-benzoylamino-Phe-4-chloro-3-(2-isothiureidoethoxy)isocoumarin and 7-Boc-valylamino-4-chloro-3-(2-isothiureidoethoxy)isocoumarin can be prepared by the same procedure.

EXAMPLE 9

Preparation of
7-(m-Carboxyphenylthiocarbamoylamino)-4-Chloro-3-(2-Isothiureidoethoxy)isocoumarin 7-(m-Carboxyphenylthiocarbamoylamino)-4-chloro-3-(2-bromoethoxy)isocoumarin was prepared from the reaction of m-carboxyphenyl isothiocyanate with 7-amino-4-chloro-3-(2-bromoethoxy)isocoumarin, yield 64%, m.p. 157°–158° C.; mass spectrum m/e 361 (M+-(COOH)PhNH+1). Anal. Calc.: C, 45.85; H, 2.84. Found: C, 45.73; H, 2.86. The bromoethoxy compound was then reacted with thiourea to give the product, yield 21%; mass spectrum (FAB+) m/e 493 (M+-Br).

EXAMPLE 10

Preparation of 7-Heptafluorobutyroylamino-4-Chloro-3-Methoxyisocoumarin

7-Amino-4-chloro-3-methoxyisocoumarin (1 eq.) and heptafluorobutyryl chloride (1.5 eq.) were dissolved in THF and then Et$_3$N (1.5 eq.) was added dropwise to the stirred mixture over a period of 4 h. After addition of Et$_3$N was completed, the reaction mixture was stirred for 20 h at r.t., then the solvent was removed in vacuo and the residue dissolved in ethyl acetate. This solution was washed with water, 10% citric acid, 4% NaHCO$_3$ and finally again with water, dried over MgSO$_4$ and evaporated. The residue was crystallized from THF-hexane to give yellow solid; yield 62%; mp 189°–190° C.; MS, m/e 421 (M+). Anal. Calc. for C$_{14}$H$_7$F$_7$ClNO$_4$: C, 39.84; H, 1.66; N, 3.32. Found: C, 40.24; H, 1.70; N, 3.33.

7-(3-fluorobenzoyl)amino-4-chloro-3-propoxyisocoumarin, 7-(4-methoxybenzoyl)amino-4-chloro-3-propoxyisocoumarin, 7-heptafluorobutyroylamino-4-chloro-3-ethoxyisocoumarin, 7-heptafluorobutyroylamino-4-chloro-3-(2-bromoethoxy)isocoumarin, 7-(3-fluorobenzoyl)amino-4-chloro-3-(2-bromoethoxy)isocoumarin, 7-(3-nitrobenzoyl)amino-4-chloro-3-(2-bromoethoxy)isocoumarin, 7-(α-toluenesulfonyl)amino-4-chloro-3-(2-bromoethoxy)isocoumarin can be prepared by the same procedure.

EXAMPLE 11

Preparation of 7-[(3-Phenylglutaryl)amino]-4-Chloro-3-Methoxyisocoumarin

One gram of 7-amino-4-chloro-3-methoxyisocoumarin dissolved in 15 ml of pyridine was treated with 4 equivalents of 3-phenylglutaric anhydride. After 5 hr, 3 ml of water were added to the reaction mixture. Partial evaporation of the solvents left a semisolid residue, which was diluted with a mixture of acetone and water (3:1), and filtered. The crude crystals were then recrystallized from acetone/water to give yellow crystals, yield 62%; mp 105°–106° C.; MS (FAB+) m/e 416 (M+). Anal. Calc. for C$_{21}$H$_{18}$ClNO$_6$·½H$_2$O: C, 57.66; H, 4.42; Cl, 3.20. Found: C, 57.60; H, 4.77; N, 3.17.

7-(o-phthalyl)amino-4-chloro-3-ethoxyisocoumarin can be prepared by the same procedure.

EXAMPLE 12

Preparation of 7-[(Methoxyglutaryl)amino]-4-Chloro-3-Methoxyisocoumarin

7-Glutarylamino-4-chloro-3-methoxyisocoumarin was prepared by the same procedure described in example 2, mp 194° C. (dec.); MS m/e 339 (M+). Anal. Calc. for C$_{15}$H$_{14}$ClNO$_6$·1.2 H$_2$O: C, 57.66; H, 4.42; N, 3.20. Found: C, 57.60; H, 4.77; N, 3.17. An ethereal solution containing 2.5 mmoles of diazomethane was added to a solution of 0.6 mmoles of 7-glutarylamino-4-chloro-3-methoxyisocoumarin in a mixture of DMF and ethyl acetate. After 30 min, the reaction mixture was evaporated to dryness and the crude ester crystallized from acetone, giving a yellow solid, mp 147°–151° C. (dec.); MS m/e 353 (M+). Anal. Calc. for C$_{16}$H$_{16}$ClNO$_6$: C, 54.30; H, 4.56; N, 3.96; Cl, 10.03. Found: C, 54.39; H, 4.58; N, 3.39; Cl, 10.13.

7-(methoxysuccinyl)amino-4-chloro-3-ethoxyisocoumarin was prepared by the same procedure.

EXAMPLE 13

Preparation of 7-[(N-Tosyl-α-phenylglycyl)amino]-4-Chloro-3-Methoxyisocoumarin

N-Tosyl phenylglycine (1.8 mmole) was dissolved in 2 ml of SOCl$_2$ and stirred at reflux temperature for 40 min. The reaction mixture was concentrated to dryness in vacuo and the residue triturated with EtOAc/Hexane (3:1) to yield the acid chloride (94%) which is used in the next step without further purification. Tosphenylglycine acid chloride (155 mg) and 7-amino-4-chloro-3-methoxyisocoumarin (72 mg) were dissolved in a mixture of methylene chloride (1 ml) and THF (1 ml). A solution of triethylamine (0.06 ml in 2 ml of CH$_2$Cl$_2$) was added dropwise and the reaction mixture was stirred at room temperature for 2 h. The solvent was removed in vacuo and the residue was triturated with ethyl acetate (1.5 ml). The resulting yellow solid was recrystallized from THF/H$_2$O to yield 108 mg (66%); mp 150°–151° C. (dec.); MS, m/e 512 (M+). Anal. Calc. for C$_{25}$H$_{21}$ClN$_2$O$_6$S: C, 58.53; H, 4.13; N, 5.46. Found: C, 58.43; H, 4.15; N, 5.40.

EXAMPLE 14

Preparation of 7-(N-Phenylcarbamoylamino)-4-Chloro-3-Methoxyisocoumarin

This compound was prepared by reaction of 110 mg (0.5 mmol) of 7-amino-4-chloro-3-methoxyisocoumarin with 60 mg (0.5 mmol) of phenyl isocyanate at room temperature in CH$_2$Cl$_2$ for 24 h. After standard workup, this isocoumarin was obtained as yellow crystals; mp 203°–204° C.; MS, m/e 344 (M+). Anal. Calc. for C$_{17}$H$_{13}$ClN$_2$O$_4$: C, 59.23; H, 3.08; N, 8.13; Cl, 10.28. Found: C, 59.28; H, 3.82; N, 8.11; Cl, 10.35.

7-benzylamino-4-chloro-3-ethoxyisocoumarin can be prepared by the same procedure.

EXAMPLE 15

Preparation of 7-Phenylthiocarbamoylamino-4-Chloro-3-Ethoxyisocoumarin

This compound was prepared by reaction of 7-amino-4-chloro-3-ethoxyisocoumarin with phenyl isothiocyanate at r. t. in THF for 24 hrs. The product was obtained as yellow solid: yield 55%, m.p. 176°–177° C. (dec.); TLC, R$_f$=0.76 (CH$_3$Cl:MeOH=9:1), MS m/e=374 (M+). Anal. Calcd. for C$_{18}$H$_{15}$N$_2$O$_3$ClS: C, 57.62; H, 4.00. Found: C, 57.77; H, 4.04.

EXAMPLE 16

Preparation of 7-Dihydrocinnamoylamino-4-Chloro-3-Propyloxyisocoumarin

This compound was synthesized by reaction of equimolar of 7-amino-4-chloro-3-propoxyisocoumarin, dihydrocinnamic acid chloride and triethylamine in dry THF. The reaction mixture was stirred at r. t. overnight, and the solution was washed with water, 4% NaHCO$_3$, water and dried over MgSO$_4$. After filtration and evaporation, a yellow residue was crystallized from THF-pentane, yield 81%; mp 182°–184° C.; TLC, R$_f$=0.74 (CH$_3$Cl:MeOH=9:1); MS, m/e 385 (M+). Anal. Calc for C$_{21}$H$_{20}$O$_4$NCl.0.5H$_2$O: C, 63.81; H, 5.32. Found: C, 63.47; H, 5.30.

7-phenoxycarbonylamino-4-chloro-3-ethoxyisocoumarin can be prepared by the same procedure.

EXAMPLE 17

Preparation of 7-(Boc-valyl)amino-4-Chloro-3-Propyloxyisocoumarin

This compound was synthesized by reaction of an equimolar amount of 7-amino-4-chloro-3-propoxyisocoumarin and Boc-Val anhydride in THF. The reaction mixture was stirred at r. t. overnight. The work-up as described above gives a yellow solid which was recrystallized from THF-pentane, yield 48%: mp 171°–173° C.; TLC, R$_f$=0.8 (CH$_3$Cl:MeOH=9:1); MS, m/e 452 (M+). Anal. Calc. for C$_{22}$H$_{29}$O$_6$N$_2$Cl: C, 58.35; H, 6.41; N, 6.19; Cl, 7.83. Found: C, 58.40; H, 6.47; N, 6.20; Cl, 7.79.

7-(Boc-phenylalanyl)amino-4-chloro-3-propyloxyisocoumarin, 7-(benzoylalanylalanyl)amino-4-chloro-3-propyloxyisocoumarin, 7-(Boc-valyl)amino-4-chloro-3-ethoxyisocoumarin and 7-(Boc-alanyl)amino-4-chloro-3-ethoxyisocoumarin can be prepared by the same procedure.

EXAMPLE 18

Preparation of 7-Ethylcarbamoylamino-4-Chloro-3-Propyloxyisocoumarin

This compound was synthesized by the reaction of an equimolar amount of 7-amino-4-chloro-3-propoxyisocoumarin and ethyl isocyanate in small amount of dry THF. The reaction mixture was stirred at r. t. for a few days. During this time the yellow crystals slowly crystallized out. After filtration, the compoumds were recrystallized once more from THF-pentane, yield 45%; mp 189°–191° C.; TLC, R$_f$=0.43 (CH$_3$Cl:MeOH=9:1); MS, m/e 324 (M+). Anal. Calc. for C$_{15}$H$_{17}$O$_4$N$_2$Cl: C, 55.42; H, 5.23. Found: C, 55.31; H, 5.28.

EXAMPLE 19

Preparation of 7-Amino-4-Chloro-3-(2-Bromoethoxy)isocoumarin

This compound was prepared by cyclization of 1 equivalent of bromoethyl nitrohomophthalate with 2.5 equivalent of PCl$_5$, followed by catalytic reduction of the nitro group. The product was yellow solid, mp 134°–137° C.; MS, m/e 317 (M+). Anal. Calc. for C$_{11}$H$_9$NO$_3$ClBr: C, 41.44; H, 2.83, N, 4.40. Found: C, 42.11; H, 2.87; N, 4.46.

EXAMPLE 20

Preparation of 7-(Phenylcarbamoylamino)-4-Chloro-3-(2-Bromoethoxy)isocoumarin

7-Amino-3-(2-bromoethoxy)-4-chloroisocoumarin was synthesized as described above. This compound (0.32 g, 1 mmole) was mixed with phenylisocyanate (0.12 g, 1 mmole) in 5 ml of THF and the reaction mixture was stirred at r. t. overnight. The product 7-(phenylcarbamoylamino)-4-chloro-3-(2-bromoethoxy)isocoumarin precipitated out, yield 40%, mp. 215°–217° C.; MS, m/e 437.9 (M+). Anal. Calc. for C$_{18}$H$_{14}$N$_2$O$_4$ClBr: C, 49.40; H, 3.22; N, 6.40; Cl, 8.10. Found: C,49.48; H, 3.25; N,6.34; Cl, 8.12.

7-(4-Fluorobenzyl)thiocarbamoylamino-4-chloro-3-(2-bromoethoxy)isocoumarin, and 7-(2,4-dimethylbenzyl)thiocarbamoylamino-4-chloro-3-(2-bromoethoxy)isocoumarin can be prepared by the same procedure.

EXAMPLE 21

Preparation of 7-(Boc-D-phenylalanylamino)-4-Chloro-3-(2-Bromoethoxy)isocoumarin Boc-D-Phe (0.33 g, 1.2 mmole) reacted with 1,3-dicyclohexylcarbodiimide (0.13 g, 0.6 mmole) in 10 ml THF at 0° C. for 1 hr to form symmetric anhydride, and then 7-amino-4-chloro-3-(2-bromoethoxy)isocoumarin (0.2 g, 0.6 mmole) was added. The reaction was stirred at r. t. overnight and 7-(Boc-D-phenylamino)-4-chloro-3-(2-bromoethoxy)isocoumarin was precipitated out (0.29 g, 71%), mp. 180°–182° C.; TLC, R$_f$=0.95 (CH$_3$Cl:MeOH=9:1); MS m/e=566 (M+). Anal. Calc. for C$_{25}$H$_{26}$N$_2$O$_6$ClBr: C, 53.07; H, 4.63; N, 4.95; Cl 6.27. Found: C,53.25; H, 4.66; N, 4.87; Cl, 6.24.

7-(Benzoyl-L-alanylamino)-4-chloro-3-(2-bromoethoxy)isocoumarin can be prepared by the same procedure.

7-(D-Phenylalanylamino)-4-chloro-3-(2-bromoethoxy)isocoumarin and 7-(alanylalanylamino)-4-chloro-3-(2-bromoethoxy)isocoumarin can be prepared by deblocking the Boc group of 7-(Boc-D-phenylalanylamino)-4-chloro-3-(2-bromoethoxy)isocoumarin and 7-(Boc-D-alanylalanylamino)-4-chloro-3-(2-bromoethoxy)isocoumarin with trifluoroacetic acid.

EXAMPLE 22

Preparation of 7-Dansylamino-4-Chloro-3-(2-Bromoethoxy)isocoumarin

Dansyl chloride (0.17 g, 0.63 mmole) was mixed with 7-amino-4-chloro-3-(2-bromoethoxy)isocoumarin (0.2 g, 0.63 mmole) in 5 ml of THF, and Et$_3$N (0.065 g) was then added. The reaction mixture was stirred at r. t. for a few days, and a yellow solid was precipitated out. The final product was crystallized from THF/hexane, yield 41%, mp 114°–117° C.; MS, m/e 552 (M++1). Anal. Calc. for C$_{23}$H$_{21}$N$_2$O$_5$ClBrS.1.5H$_2$O: C, 47.63; H, 4.14. Found: C, 47.41; H, 4.27.

7-(p-Toluenesulfonyl)amino-4-chloro-3-(2-bromoethoxy)isocoumarin can be prepared by the same procedure.

EXAMPLE 23

Preparation of 7-(Biotinylamino)-4-Chloro-3-(2-Phenylethoxy)isocoumarin

Biotin acid chloride was prepared by incubating 0.4 g of biotin in 6 ml of thionyl chloride at 25°–35° C. for 1 hr, and excess thionyl chloride was removed under vacuum. The acid chloride was used for the next step without further purification. Biotin acid chloride and 7-amino-4-chloro-3-(2-phenylethoxy)isocoumarin (0.26 g) was dissolved in small amount of DMF, and then Et$_3$N (0.08 g) were added. The reaction mixture was stirred at r. t. overnight. The product was purified by column chromatography, yield 0.1 g, mp 182°-185° C.; TLC, $R_f$=0.25 (CH$_2$Cl$_2$:MeOH=15:1). Anal. Calc for C$_{27}$H$_{28}$N$_3$O$_5$ClS.0.25H$_2$O: C, 59.39; H, 5.22, N, 7.70. Found: C, 59.08; H, 5.37; N, 7.94.

7-(Biotinylamino)-4-chloro-3-(pentafluoropropoxy)isocoumarin can be prepared by the same procedure.

EXAMPLE 24

Preparation of 7-[(6-Biotinylamino)caproyl]amino-4-Chloro-3-(2-Phenylethoxy)isocoumarin 6-(Biotinylamino)caproic acid was prepared from N-hydroxysuccinimido biotinate (Jasiewicz et al., Exp. Cell Res. 100, pp 213–217 (1976)) and methyl 6-aminocaproic acid hydrochloride by a previously described method (Hoffmann et al., Biochemistry 23, pp 2547–2553 (1984)). 6-(Biotinylamino)caproic acid chloride was synthesized and reacted with 7-amino-4-chloro-3-(2-phenylethoxy)isocoumarin as described above. The product was purified by column chromatography, mp 163°-167° C. Anal. Calc. for C$_{33}$H$_{39}$N$_4$O$_6$ClS.H$_2$O: C, 58.72; H, 6.22; N, 8.96; Cl, 5.59. Found: C, 58.87; H, 6.14; N, 8.32; Cl, 5.27.

TABLE I

Inactivation Rates for Inhibition of Trypsin-Like Serine Proteases by Substituted Isocoumarins[a]

| Inhibitors | $k_{obs}$/[I] (M$^{-1}$s$^{-1}$) | | | | | | | | |
|---|---|---|---|---|---|---|---|---|---|
| | bovine thrombin[b] | bovine factor Xa[c] | human factor Xa[d] | porcine pancreatic kallikrein[e] | human plasma kallikrein[g] | human factor XIa[g] | human factor XIIa[h] | bovine trypsin[i] | human factor VIIa[j] |
| 3-(3-aminopropoxy)-isocoumarin | 3.0 | NI[k] | | 5.0 | 30 | 30 | 3.0 | 1,200 | |
| 3-(3-aminopropoxy)-4-chloroisocoumarin | 350 | 160 | | 860 | 1,400 | 380 | 190 | 7,600 | |
| 3-(2-isothiureidoethoxy)-4-chloroisocoumarin | 4,700 | 5,600 | | 12,000 | 280,000[l] | 44,000 | 39,000 | 32,000 | |
| 3-(3-isothiureidopropoxy)-4-chloroisocoumarin | 1,430 | 220 | | 19,000 | >110,000[l] | 47,000 | 27,000 | 46,000 | 450 |
| 7-amino-3-(3-isothiureidopropoxy)-4-chloroisocoumarin | 630 | 1,640 | 60 | >110,000[m] | 1,100 | 22,000 | 6,200 | 410,000[n] | 430 |
| 7-guanidino-3-methoxy-isocoumarin | 4,900 | 460 | | 1,900 | 13,000 | 1,400 | 520 | 3,300 | |
| 7-guanidino-3-methoxy-4-chloroisocoumarin | 290,000[n] | 3,100 | 11,000 | 45,000[n] | 240,000[n] | 36,200 | 20,000 | 310,000[n] | |
| 7-guanidino-3-ethoxy-isocoumarin | 3,700 | 2,700 | | 16,000 | 44,000 | 3,100 | 1,300 | 20,000 | |
| 7-guanidino-3-ethoxy-4-chloroisocoumarin | >55,000[m] | 26,700 | 11,000 | >200,000[m] | >500,000[l] | 60,000 | 22,000 | >110,000[m] | 2,200 |
| 7-guanidino-3-(2-phenylethoxy)isocoumarin | 5,700 | 11,000 | | 16,000 | 62,000 | 1,200 | 690 | 45,000 | |
| 7-guanidino-3-(2-phenylethoxy)-4-chloroisocoumarin | >30,000[m] | 96,000 | 11,000 | 200,000[m] | >270,000[l] | 20,000 | 26,000 | >110,000[m] | |
| 7-(glycylamino)-3-methoxy-4-chloroisocoumarin | 51.5 | NI | | | | | | 32,100 | |
| 7-(alanylamino)-3-methoxy-4-chloroisocoumarin | NI | NI | | | | | | 470 | |

[a]Conditions were as 0.1M Hepes, 0.01M CaCl$_2$, pH 7.5 and 8–12% Me$_2$SO and 25° C. Rate constants were measured by incubation method unless otherwise noted. An aliquot of inhibitor was added to an enzyme solution and aliquots removed with time and assayed for remaining enzymatic activity. First-order rate constants, k$_{obs}$ were obtained from the plots of ln(v$_t$/v$_o$) versus time.
[b]Inhibitor concentrations were from 0.3 to 400 μM.
[c]Inhibitor concentrations were from 0.4 to 310 μM.
[d]Inhibitor concentrations were from 5 to 105 μM.
[e]Inhibitor concentrations were from 0.4 to 300 μM.
[f]Inhibitor concentrations were from 0.3 to 300 μM.
[g]Inhibitor concentrations were from 3 to 330 μM.
[h]Inhibitor concentrations were from 3 to 330 μM.
[i]Inhibitor concentrations were from 1 to 12 μM.
[j]Inhibitor concentrations were from 5 to 44 μM.
[k]No inhibition.
[l]Inactivation was extremely rapid, and the k$_{obs}$/[I] values were based on the residual enzymatic activity at 0.2 min.
[m]Second-order rate constant was obtained from same concentration of enzyme and inhibitor.
[n]Inactivation rate constants were obtained by progress curve method described by Tian and Tsou, Biochemistry 21, 1028–1032 (1982).

TABLE II

Inactivation Rates of Inhibition of Complement Proteins by Substituted Isocoumarins and APMSF[a]

| Inhibitors | $k_{obs}$/[I] (M$^{-1}$s$^{-1}$) | | | | | |
|---|---|---|---|---|---|---|
| | D[b] | C2[c] | C2a[c] | B[c] | Bb[d] | C1s[e] | C1r[f] |
| APMSF | 110 | NI[g] | NI | NI | NI | | |
| 3,4-dichloroisocoumarin | 192 | NI | NI | NI | NI | 170 | 42 |
| 3-ethoxy-4-chloroisocoumarin | 0.25 | NI | NI | NI | NI | | |
| 7-amino-3-methoxy-4-chloroisocoumarin | 1.3 | NI | NI | NI | NI | | |
| 3-(2-isothiureidoethoxy)-4-chloroisocoumarin | 61 | 1.5 | 1.4 | 13 | 15 | | |
| 3-(3-isothiureidopropoxy)-4-chloroisocoumarin | 145 | 0.5 | 0.8 | 0.4 | 0.8 | 130,000 | 6,610 |
| 7-amino-3-(3-isothiureidopropoxy)-4-chloroisocoumarin | 55 | NI | | | NI | 23,000 | 1,320 |
| 7-guanidino-3-methoxy-4-chloroisocoumarin | 252 | NI | | 285 | 74 | 660 | 75 |
| 7-guanidino-3-ethoxy-4-chloroisocoumarin | 193 | NI | | 167 | 95 | 690 | 239 |

TABLE II-continued

Inactivation Rates of Inhibition of Complement Proteins by Substituted Isocoumarins and APMSF[a].

| Inhibitors | $k_{obs}/[I]$ (M$^{-1}$s$^{-1}$) | | | | | | |
|---|---|---|---|---|---|---|---|
| | D[b] | C2[c] | C2a[c] | B[c] | Bb[d] | C1s[e] | C1r[f] |
| 7-guanidino-3-(2-phenylethoxy)-4-chloroisocoumarin | 92 | NI | | | 58 | 90 | 342 |

[a]Conditions were 0.1M Hepes, 0.5M NaCl, pH 7.5, 8–10% Me$_2$SO and 25° C. Inactivation rates were measured by incubation method. Enzyme concentrations were as follows: protein D, 1–9 μM; C2, 0.7–1 μM; B, 1.8 μM; Bb, 0.3–0.8 μM; C1s, 0.07 μM; C1r, 0.51 μM.
[b]Inhibitor concentrations were from 0.05 mM to 1.29 mM.
[c]Inhibitor concentrations were from 0.19 mM to 1.25 mM.
[d]Inhibitor concentrations were from 0.05 mM to 1.25 mM.
[e]Inhibitor concentrations were from 0.8 μM to 44 μM.
[f]Inhibitor concentrations were from 4.6 μM to 470 μM.
[g]No inhibition.

TABLE III

The Inactivation Rates of Sheep Lung Lymph Tryptase[a], Human Lung Tryptase[a] and Rat Skin Tryptase[b] by Substituted Isocoumarins.

| Inhibitors | $k_{obs}/[I]$ (M$^{-1}$s$^{-1}$) | | |
|---|---|---|---|
| | S.L. Tryptase[c] | H.L. Tryptase[d] | R.S. Tryptase[e] |
| 3,4-dichloroisocoumarin | 39 | 185 | 610 |
| 3-(3-aminopropoxy)isocoumarin | 8.1 | | |
| 3-(3-aminopropoxy)-4-chloroisocoumarin | 18 | 2,000 | 8,370 |
| 3-(2-isothiureidoethoxy)-4-chloroisocoumarin | 290 | | |
| 3-(3-isothiureidopropoxy)-4-chloroisocoumarin | 230 | 64,000 | 53,000 |
| 7-amino-3-(3-isothiureidopropoxy)-4-chloroisocoumarin | 710 | 28,000 | 63,000 |
| 7-guanidino-3-methoxyisocoumarin | 53 | | |
| 7-guanidino-3-methoxy-4-chloroisocoumarin | 620 | 20,000 | 52,000 |
| 7-guanidino-3-ethoxyisocoumarin | 150 | | |
| 7-guanidino-3-ethoxy-4-chloroisocoumarin | 2,200 | 61,000 | 82,000 |
| 7-guanidino-3-(2-phenylethoxy)isocoumarin | 150 | | |
| 7-guanidino-3-(2-phenylethoxy)-4-chloroisocoumarin | 3,900 | 56,000 | 86,000 |
| APMSF[f] | 230 | | |

[a]Inactivation rates were measured at 0.1M Hepes, 0.5M NaCl, pH 7.5 buffer, 8% Me$_2$SO and 25° C.
[b]Inactivation rates were measured at 25 mM phosphate, 0.5M NaCl, 1 mM EDTA, pH 7.5 buffer, 9% Me$_2$SO and 25° C.
[c]Inhibitor concentrations were from 10 μM to 460 μM.
[d]Inhibitor concentrations were from 0.4 μM to 50 μM.
[e]Inhibitor concentrations were from 0.4 μM to 50 μM.
[f]The inhibition rate was measured at 0.1M Hepes, 0.5M NaCl, pH 7.0, 25° C.

TABLE IV

Inactivation Rates for Inhibition of Serine Proteases by Substituted Isocoumarins[a]

| Inhibitors | $k_{obs}/[I]$ (M$^{-1}$s$^{-1}$) | | | |
|---|---|---|---|---|
| | PPE[b] | HLE[c] | Chymotrypsin[d] | Cathepsin G[e] |
| 3-(3-aminopropoxy)isocoumarin | 2.3 | 47 | 38 | 2.8 |
| 3-(3-aminopropoxy)-4-chloroisocoumarin | 70 | 860 | 580 | 260 |
| 3-(2-isothiureidoethoxy)-4-chloroisocoumarin | 270 | 220 | 1,300 | 110 |
| 3-(3-isothiureidopropoxy)-4-chloroisocoumarin | 70 | 2,000 | 1,700 | 83 |
| 7-amino-3-(3-isothiureidopropoxy)-4-chloroisocoumarin | 1.0 | 130 | 1,600 | 36 |
| 7-guanidino-3-methoxyisocoumarin | 55 | 320 | 270 | —[f] |
| 7-guanidino-3-methoxy-4-chloroisocoumarin | 860 | 6,400 | 7,200 | 11,000 |
| 7-guanidino-3-ethoxyisocoumarin | 86 | 1,900 | 990 | —[g] |
| 7-guanidino-3-ethoxy-4-chloroisocoumarin | 2,300 | 81,000 | 37,000 | 84,000 |
| 7-guanidino-3-(2-phenylethoxy)isocoumarin | NI[h] | 0.9 | 2,600 | —[i] |
| 7-guanidino-3-(2-phenylethoxy)-4-chloroioscoumarin | 5.7 | 73 | 38,000 | 66,000 |
| 7-(glycylamino)-3-methoxy-4-chloroisocoumarin | 1,960 | 7,710 | | 4.9 |
| 7-(alanylamino)-3-methoxy-4-chloroisocoumarin | 1,610 | 13,500 | | 20 |

[a]Inactivation rates were measured at 0.1M Hepes, 0.5 NaCl, pH 7.5, 8–12% Me$_2$SO and 25° C. by incubation method. An aliquot of inhibitor was added to a solution of enzyme and aliquots removed with time and assayed for remaining activity.
[b]Inhibitor concentrations were from 0.01 to 0.51 mM.
[c]Inhibitor concentrations were from 0.001 to 0.18 mM.
[d]Inhibitor concentrations were from 0.004 to 0.33 mM.
[e]Inhibitor concentrations were from 0.002 to 0.35 mM.
[f]Inhibition was not time dependent, 81% inhibition was obtained at 0.49 mM.
[g]Inhibition was not time dependent, 87% inhibition was obtained at 47 μM.
[h]No inhibition.
[i]Inhibition was not time dependent, 87% inhibition was obtained at 0.53 mM.

TABLE V

Inactivation Rates for Inhibition of Chymases by Substituted Isocoumarins[a].

| Inhibitors | $k_{obs}/[I]$ (M$^{-1}$s$^{-1}$) | | |
|---|---|---|---|
| | Rat Mast Cell Protease II[b] | Human Skin Chymase[c] | Human Lung Chymase[d] |
| 7-guanidino-3-ethoxy-4-chloroisocoumarin | 1100 | 33 | 540 |
| 7-guanidino-3-(2- | 4100 | 22 | — |

TABLE V-continued

Inactivation Rates for Inhibition of Chymases by Substituted Isocoumarins[a].

| Inhibitors | Rat Mast Cell Protease II[b] | Human Skin Chymase[c] | Human Lung Chymase[d] |
|---|---|---|---|
| phenylethoxy)-4-chloroisocoumarin | | | |

[a]Inactivation rates were measured at 0.1M Hepes, 0.5M NaCl, pH 7.5, 8–12% Me$_2$SO and 25° C. by incubation method. An aliquot of inhibitor was added to a solution of enzyme and aliquots were removed with time and assayed for the remaining activity.
[b]Inhibitor concentration were from 0.007 mM to 0.013 mM.
[c]Inhibitor concentration were from 0.41 mM to 0.53 mM.
[d]Inhibitor concentration was 0.38 mM.

TABLE VI

Inactivation of Human Plasmin and Recombinant Human Tissue Plasminogen Activator by Substituted Isocoumarins[a].

| Inhibitor | Plasmin[b] | Plasminogen Activator[c] |
|---|---|---|
| 3,4-dichloroisocoumarin | | 73 |
| 3-(3-aminopropoxy)isocoumarin | 36 | |
| 3-(3-aminopropoxy)-4-chloro-isocoumarin | 770 | 94 |
| 3-(3-isothiureidopropoxy)-4-chloro-isocoumarin | | 4,690 |
| 7-amino-3-(3-isothiureido-propoxy)-4-chloroisocoumarin | 4,340 | 5,690 |
| 7-guanidino-3-methoxyisocoumarin | 320 | |
| 7-guanidino-3-methoxy-4-chloro-isocoumarin | 3,500 | 4,420 |
| 7-guanidino-3-ethoxy-4-chloro-isocoumarin | 12,320 | 7,720 |
| 7-guanidino-3-(2-phenylethoxy)-4-chloroisocoumarin | 4,140 | 6,780 |
| 7-(glycylamino)-3-methoxy-4-chloroisocoumarin | 1,470 | |
| 7-(alanylamino)-3-methoxy-4-chloroisocoumarin | 31 | |

[a]Inactivation constants were measured at 0.1M Hepes, 0.5M NaCl (or 0.01M CaCl$_2$), pH 7.5, 8–12% Me$_2$SO and 25° C.
[b]Inhibitor concentrations were from 4 μM to 330 μM.
[c]Inhibitor concentrations were from 7 μM to 44 μM.

TABLE VII

Inactivation Rates of Mouse Granzyme A, Human Granzyme A and Q-31 Tryptase by Substituted Isocoumarins[a].

| Inhibitors | Mouse Granzyme A[b] | Human Granzyme A[b] | Human Q-31 Tryptase[c] |
|---|---|---|---|
| 3,4-dichloro-isocoumarin | 50 | 50 | 29 |
| 3-(3-aminopropoxy)-4-chloro-isocoumarin | 770 | 2,010 | |
| 3-(3-isothiureido-propoxy)-4-chloro-isocoumarin | 17,500 | 18,420 | 12,830 |
| 7-amino-3-(3-isothiureido-propoxy)-4-chloroisocoumarin | 3,000 | 6,750 | 1,960 |
| 7-guanidino-3-methoxy-4-chloro-isocoumarin | 15,000 | | 6,620 |
| 7-guanidino-3-ethoxy-4-chloro-isocoumarin | 26,200 | 6,850 | 6,180 |
| 7-guanidino-3-(2-phenylethoxy)-4-chloro-isocoumarin | 6,400 | | 1,880 |

[a]Inactivation rates were measured at 0.1M Hepes, 0.01M CaCl$_2$, pH 7.5, 8% Me$_2$SO and 25° C. by incubation method. Z-Arg-SBzl (74–85 μM) was used as the substrate to monitor the residual enzymatic activity.
[b]Inhibitor concentrations were from 0.4 μM to 45 μM.
[c]Inhibitor concentrations were from 3 μM to 500 μM.

TABLE VIII

Inhibition Rates of Bovine Trypsin and Coagulation Enzymes by 7-Substituted-4-chloro-3-isothiureidoalkoxyisocoumarins[a].

| Compounds | Bovine Trypsin[b] | Bovine Thrombin[c] | Human Thrombin[d] | Human Factor Xa[e] | Human Factor XIa[f] | Human Factor XIIa[g] |
|---|---|---|---|---|---|---|
| NH$_2$-CiTPrOIC | 410,000[h] | 630[h] | 760 | 60[h] | 22,000[h] | 6,200[h] |
| PhCH$_2$NHCONH-CiTPrOIC | 51,000 | 420 | 700 | | | |
| PhNHCONH-CiTPrOIC | 63,000 | 970 | 1,840 | 50 | | 7,720 |
| CH$_3$CONH-CiTPrOIC | 107,000 | 420 | 310 | | | |
| PhCH$_2$CH$_2$CONH-CiTPrOIC | 87,900 | 820 | 630 | | | |
| PhCH$_2$CONH-CiTPrOIC | 165,000 | 600 | 610 | | | |
| L-Phe—NH-CiTPrOIC | | 400 | 470 | | | |
| Boc-L-Phe—NH-CiTPrOIC | | 330 | 520 | | | |
| D-Phe—NH-CiTPrOIC | 68,300 | 180 | 220 | | | |
| Boc-D-Phe—NH-CiTPrOIC | 105,000 | 190 | 230 | | | |
| Ph—NH—CO—NH-CiTEtOIC | 21,000 | 25,000 | 22,400 | 4,740 | 104,000 | 50,000 |
| PhCH$_2$NHCONH-CiTEtOIC | | 16,800 | 11,680 | 2,340 | 105,000 | 45,000 |
| PhCH$_2$CONH-CiTEtOIC | | 15,800 | 6,730 | 3,630 | | 59,000 |
| D-Phe—NH-CiTEtOIC | | 4,240 | 3,070 | 3,070 | | 82,000 |
| Boc-D-Phe—NH-CiTEtOIC | | 1,040 | 1,090 | | | |
| L-Phe—NH-CiTEtOIC | | 1,280 | 1,340 | 3,770 | | 107,000 |
| Boc-L-Phe—NH-CiTEtOIC | | 1,090 | 1,140 | 1,620 | | |
| Ala—Ala—NH-CiTEtOIC | | 1,070 | 880 | 1,490 | | |
| Boc—Ala—Ala—NH-CiTEtOIC | | 1,530 | 970 | | | |
| (CH$_3$)$_2$CHNHCONH-CiTEtOIC | | 4,100 | 5,000 | | | |
| Naphthyl-NHCONH-CiTEtOIC | | 17,500 | 5,800 | | | |
| S-C$_6$H$_5$(CH$_3$)CHNHCONH-CiTEtOIC | | 41,300 | 21,000 | | | |
| R-C$_6$H$_5$(CH$_3$)CHNHCONH-CiTEtOIC | | 29,500 | 12,000 | | | |
| PhNHCSNH-CiTEtOIC | | | 21,400 | | | |

TABLE VIII-continued

Inhibition Rates of Bovine Trypsin and Coagulation Enzymes by 7-Substituted-4-chloro-3-isothiureidoalkoxyisocoumarins[a].

| | $k_{obs}/[I]$ $(M^{-1}s^{-1})$ | | | | | |
|---|---|---|---|---|---|---|
| Compounds | Bovine Trypsin[b] | Bovine Thrombin[c] | Human Thrombin[d] | Human Factor Xa[e] | Human Factor XIa[f] | Human Factor XIIa[g] |
| m-Carboxy-PhNHCSNH-CiTEtOIC | | | 17,500 | | | |

[a]Inhibition rates were measured in 0.1M Hepes, 0.01M CaCl$_2$, pH 7.5 buffer, 8% Me$_2$SO and at 25° C.
[b]Inhibitor concentration were 1.1–4.6 μM.
[c]Inhibitor concentration were 1.2–54 μM.
[d]Inhibitor concentration were 1.2–54 μM.
[e]Inhibitor concentration were 3.6–44 μM.
[f]Inhibitor concentration were 0.7–0.8 μM.
[g]Inhibitor concentration were 3.6–4.9 μM.
[h]Data was obtained from Kam, Fujikawa, and Powers Biochemistry 27, pp 2547–2557.(1988).

TABLE IX

Inhibition of Several Tryptases by 7-Substituted-4-chloro-3-isothiureidoalkoxyisocoumarins[a].

| | $k_{obs}/[I]$ $(M^{-1}s^{-1})$ | | | | |
|---|---|---|---|---|---|
| Compounds | Human Skin Tryptase[b] | Rat Skin Tryptase[c] | Human Lung Tryptase[d] | Human Plasmin[e] | Human r-t-PA[f] |
| NH$_2$-CiTPrOIC | | 39,000 | 19,000 | | 13,000 |
| PhCH$_2$NHCONH-CiTPrOIC | 68%[g] | 270,000 | 190,000 | 5,120 | 18,000 |
| PhNHCONH-CiTPrOIC | 38,000 | 250,000 | 140,000 | | 19,000 |
| CH$_3$CONH-CiTPrOIC | | 99,000 | 60% | | 7,000 |
| PhCH$_2$CH$_2$CONH-CiTPrOIC | | 170,000 | 180,000 | | 15,000 |
| PhCH$_2$CONH-CiTPrOIC | | 145,000 | 140,000 | | 9,000 |
| L-Phe—NH-CiTPrOIC | | 96,000 | 54% | | 11,000 |
| Boc-L-Phe—NH-CiTPrOIC | | 150,000 | 170,000 | | 6,000 |
| PhNHCONH-CiTEtOIC | | 170,000 | 170,000 | 32,000 | 16,000 |
| PhCH$_2$NHCONH-CiTEtOIC | | 200,000 | 280,000 | | 19,000 |
| PhCH$_2$CONH-CiTEtOIC | | 120,000 | 110,000 | | 64%[g] |
| D-Phe—NH-CiTEtOIC | 62,000 | 360,000 | 60,000 | | 15,000 |
| Boc-D-Phe—NH-CiTEtOIC | | 135,000 | 44%[g] | | 65%[g] |
| L-Phe—NH-CiTEtOIC | | 650,000 | 260,000 | | 13,000 |
| S-C$_6$H$_5$(CH$_3$)CHNHCONH-CiTEtOIC | | | | 27,800 | |

[a]Inhibition rates were measured in 0.1M Hepes, 0.01M CaCl$_2$, pH 7.5 buffer for human plasmin; 25 mM Phosphate, 0.5M NaCl, 1 mM EDTA, pH 7.5 buffer for rat skin tryptase and 0.1M Hepes, 0.5M NaCl, pH 7.5 for human lung tryptase, human skin tryptase and r-t-PA. All enzymes were assayed with Z-Arg-SBzl (0.07 mM) in the presence of 4,4'-dithiodipyridine (0.33 mM). Reaction mixtures contained 8% Me$_2$SO and assays were performed at 25° C.
[b]Inhibitor concentrations were 0.34–0.39 μM.
[c]Inhibitor concentrations were 0.42–0.51 μM
[d]Inhibitor concentrations were 0.42–0.47 μM.
[e]Inhibitor concentrations were 8.3–41 μM.
[f]Inhibitor concentrations were 3.5–5.0 μM, r-t-PA = recombinant-tissue plasminogen activator.
[g]Inhibition was not time dependent and the percentage was measured at 0.34–5.0 μM.

TABLE X

Inhibition of Serine Proteases by 7-Substituted-4-chloro-3-isothiureidoalkoxyisocoumarins[a].

| | $k_{obs}/[I]$ $(M^{-1}s^{-1})$ | | | |
|---|---|---|---|---|
| Compounds | PPE[b] | HLE[c] | Chymotrypsin[d] | Cathepsin G[b] |
| PhCH$_2$NHCONH-CiTPrOIC | 9%[e] | 250 | 13,430 | 50 |
| CH$_3$CONH-CiTPrOIC | NI[f] | 200 | 5,200 | 31 |
| PhCH$_2$CONH-CiTPrOIC | NI | 130 | 260,000[g] | 64 |
| PhNHCONH-CiTEtOIC | 840 | 46,000[h] 5,730 | 16,000 | 100 |
| Boc-D-Phe—NH-CiTEtOIC | 12%[f] | 3,100 | 220 | 35 |
| L-Phe—NH-CiTEtOIC | NI | NI | 8,400 | 53 |
| S-C$_6$H$_5$(CH$_3$)CHNHCONH-CiTEtOIC | 21%[f] | 5,100[h] 360 | 260 | 35 |
| R-C$_6$H$_5$(CH$_3$)CHNHCONH-CiTEtOIC | 9%[f] | 40%[i] | 360 | 145 |

[a]Inhibition rates were measured in 0.1M Hepes, 0.05M NaCl, pH 7.5 buffer, 8–9% Me$_2$SO and at 25° C. Substrates were Suc—Ala—Ala—Ala—NA (0.48 mM) for PPE; MeO—Suc—Ala—Ala—Pro—Val—NA (0.24 mM) for HLE; Suc—Val—Pro—Phe—NA (0.48 mM) for chymotrypsin and cathepsin G.
[b]Inhibitor concentrations were 33–46 μM.
[c]Inhibitor concentrations were 2.1–42 μM.
[d]Inhibitor concentrations were 0.9–43 μM.
[e]Percentage of inhibition was obtained after 20 min incubation of enzyme with inhibitor.
[f]No inhibition.
[g]Second order of rate constant was obtained at equal molar concentrations of enzyme and inhibitor.
[h]Inhibition was biphasic.
[i]Percentage of inhibition was obtained after 5 min incubation of enzyme with inhibitor.

TABLE XI

Inhibition Constants for Inactivation of Elastases by 7-substituted-4-chloro-3-alkoxyisocoumarins[a].

| Compounds 7-Substituent | HLE [I] (μM) | HLE $k_{obs}/[I]$ $(M^{-1}s^{-1})$ | PPE [I] (μM) | PPE $k_{obs}/[I]$ $(M^{-1}s^{-1})$ |
|---|---|---|---|---|
| 7-substituted-4-chloro-3-methoxyisocoumarin | | | | |
| NCO | 1.8 | 9,200 | 8.3 | 650 |
| EtOCONH | 2.3 | 47,000 | 8.3 | 2,000 |
| PhOCONH | 1.8 | 13,000 | 8.8 | 850 |
| PhCH$_2$OCONH | 1.6 | 71,000 | 136.0 | 260 |
| H$_2$NCONH | | | 8.2 | 2,100 |
| CH$_3$NHCONH | 3.3 | 9,460 | 13 | 1,300 |
| EtNHCONH | | | 6.3 | 1,700 |
| i-PrNHCONH | 3.0 | 9,000 | 12 | 2,300 |
| i-BuNHCONH | 6.6 | 20,000 | 13 | 3,200 |
| PhNHCONH | 2.0 | 49,000 | 8.3 | 7,300 |
| PhCH$_2$(PhCH$_2$CH$_2$)NCONH | 2.2 | 12,000 | 490.0 | 17 |
| C$_3$F$_7$CONH | 2.7 | 47,000 | 17.0 | 1,100 |
| Fmoc-NH | 2.5 | 10,000 | 600.0 | 20 |
| Tos-Phenylglycyl-NH | 1.6 | 84,000 | 8.3 | 1,500 |
| o-HOOCC$_6$H$_4$CONH | 1.8 | 52,000 | 17.0 | 2,700 |
| o-CH$_3$OOCC$_6$H$_4$CONH | — | — | 8.3 | 7,100 |
| CH$_3$OOCCH$_2$CH$_2$CONH | 2.3 | 43,000 | 17.0 | 2,200 |
| CH$_3$OOCCH$_2$CH$_2$CH$_2$CONH | 2.3 | 54,000 | 8.3 | 2,800 |
| HOOCCH$_2$CH(Ph)CH$_2$CONH | 1.6 | 66,000 | 8.3 | 3,100 |
| m-CH$_3$OOCNHC$_6$H$_4$CONH | 1.4 | 100,000 | 17.0 | 2,500 |
| 7-substituted-4-chloro-3-ethoxyisocoumarin | | | | |
| EtO—CO—NH | | | 9.6 | 3,500 |
| Et—NH—CS—NH | | | 20–50 | 4,200 |
| Ph—NH—CS—NH | | | 9–31 | 12,000 |

[a]Inhibition constants were in 0.1M Hepes, 0.5M NaCl, pH 7.5 buffer, 8–9% Me$_2$SO and at 25° C.

TABLE XII

Inhibition Rates of Inactivation of Serine Proteases by Derivatives of 7-Substituted-4-chloro-3-propyloxyisocoumarins[a].

| Compounds 7-Substituent | $k_{obs}/[I](M^{-1}s^{-1})$ PPE[b] | HLE[c] | Chymotrypsin[d] | Cathepsin G[e] |
|---|---|---|---|---|
| PhCH$_2$CH$_2$CONH | 220 | >250,000 | 12,000 | 20 |
| CH$_3$CH$_2$OCONH | 1,600 | >181,000 | 5,200 | 138 |
| CH$_3$CH$_2$NHCONH | 80 | >276,000 | 120 | 166 |
| PhNHCONH | 520 | 143,000 | 6,100 | NI |
| PHNHCSNH | | >166,000 | | |
| PhCH$_2$NHCSNH | | >131,000 | | |
| 3-NO$_2$—C$_6$H$_4$CONH | | >210,000 | | 4 |
| CH$_3$SCH$_2$CONH | | >152,000 | | 28 |
| Boc—Val—NH | | 64,000 | | 17 |

[a]Inhibition rates were measured in 0.1M Hepes, 0.5M NaCl, 2.5% Me$_2$SO, pH 7.5 and at 25° C.
[b]Inhibitor concentrations were 34–56 μM.
[c]Inhibitor concentrations were 0.7–1.9 μM.
[d]Inhibitor concentrations were 3.4–70 μM.
[e]Inhibitor concentrations were 8.7–87 μM.

TABLE XIII

Inhibition of Serine Proteases by Biotin-Isocoumarin Derivates[a].

| Compounds | $k_{obs}/[I](M^{-1}s^{-1})$ Chymotrypsin[b] | Cat. G[c] | HLE[d] | PPE[e] |
|---|---|---|---|---|
| 7-biotinylamino-4-chloro-3-2(2-phenylethoxy)isocoumarin | 330 165 | NI | 740 | NI |
| 7-biotinylamino-4-chloro-3-propoxyisocoumarin | 65 | 6.7 | 19,900 | 470 |
| 7-(6-biotinylaminocaproyl)amino-4-chloro-3-(2-phenylethoxy)isocoumarin | 1,080 190 | 13% | 670 | NI[f] |
| 7-(6-biotinylaminocaproyl)amino-4-chloro-3-propoxyisocoumarin | 260 | 3.3 | 76,700 | 350 |
| 7-(6-biotinylaminocaproyl)amino-4-chloro-3-ethoxyisocoumarin | 260 | 59 | 96,000 | 520 |

[a]Inhibition was measured in 0.1M Hepes, 0.5M NaCl, pH 7.5 buffer, 5–10% Me$_2$SO and at 25° C. Suc—Val—Pro—Phe—NA (0.48 mM) was used as the substrate for chymotrypsin and cat G. MeO—Suc—Ala—Ala—Pro—Val—NA (0.24–0.47 mM) and Suc—Ala—Ala—Ala—NA (0.29–0.48 mM) were used as the substrate for HLE and PPE respectively.
[b]Inhibitor concentrations were 20–400 μM.
[c]Inhibitor concentrations were 75–400 μM.
[d]Inhibitor concentrations were 2.0–78 μM.
[e]Inhibitor concentrations were 38–78 μM.
[f]No inhibition.

TABLE XIV

Inhibition of Rat granule Serine Proteases by Biotin-Isocoumarin Derivatives[a].

| Compounds | [I] (mM) | Rat Granule Chymase % of inhibition[b] | Rat Granule Tryptase $k_{obs}$/[I] (M$^{-1}$s$^{-1}$) |
|---|---|---|---|
| 7-(6-Biotinylaminocaproyl)amino-4-chloro-3-(2-phenylethoxy)isocoumarin | 0.078 | 30–50 | 6–12 |
| 7-Biotinylamino-4-chloro-3-(2-phenylethoxy)isocoumarin | 0.2 | 10–20 | 2–3 |

[a]Inhibition was measured at 0.1M Hepes, 0.5M NaCl, pH 7.5 buffer, 10% Me$_2$SO and 25° C. Suc—Phe—Leu—Phe-SBzl (0.14 mM) and Z-Gly—Arg-SBzl (0.06 mM) were used to measure chymase and tryptase activity respectively.
[b]Inhibition was not time dependent.

TABLE XV

Reactivation of Inhibited Chymotrypsin and Rat Granule Chymase by Biotin-Isocoumarin Derivatives in Buffer and in the Presence of NH$_2$OH[a].

| | | % of Enzyme Activity Reactivated | | |
|---|---|---|---|---|
| | | Chymotrypsin | | |
| Inhibitor | [I] (μM) | in buffer[b] | +NH$_2$OH | Rat granule chymase +NH$_2$OH |
| 7-(6-Biotinylaminocaproyl)amino-4-chloro-3-(2-phenylethoxy)isocoumarin | 39 | 6 | 50 | 30–50 |
| | 78 | 0 | 40 | |
| 7-Biotinylamino-4-chloro-3-(2-phenylethoxy)isocoumarin | 39 | 51 | 85 | 100 |
| | 78 | 7 | 79 | |

[a]Inhibition was performed at 0.1M Hepes, 0.5M NaCl, pH 7.5 buffer, 10% Me$_2$SO and 25° C. Reactivation was carried out in the presence of 0.36M of NH$_2$OH, and occurred immediately after the addition of NH$_2$OH.
[b]Enzyme activity was measured after two days.

TABLE XVI

Inhibition Rates of Serine Proteases by 7-substituted-4-chloro-3-bromoalkoxyisocoumarins and 7-amino-4-chloro-3-alkoxyisocoumarins[a].

| | $k_{obs}$/[I] (M$^{-1}$s$^{-1}$) | | | |
|---|---|---|---|---|
| Compounds | PPE[b] | HLE[c] | Chymotrypsin[d] | Cathepsin G[e] |
| (I) 7-substituted-4-chloro-3-(2-bromoethoxy)isocoumarin | | | | |
| 7-NH$_2$ | 1,000 | 200,000[f] | 1,160 | 410 |
| 7-NO$_2$ | 6,330 | 65,600 | 98,000[g] | 710 |
| 7-(t-Bu—NH—CO—NH) | 6,600 | | 320 | 56 |
| 7-(isopropyl-NH—CO—NH) | 4,470 | 646,000[g] | 1340[h] 380[h] | 77 |
| 7-(Ph—NH—CO—NH) | 36 | 1,200,000[g] | 12 | NI[i] |
| 7-(Ph—CH$_2$—NH—CO—NH) | 3,010 | 480,000[g] | 890 | 23%[j] |
| 7-(R-(C$_6$H$_5$)(CH$_3$)CH—NH—CO—NH) | 9,900 | >440,000[g] | 180[h] 90[h] | 77 |
| 7-(S-(C$_6$H$_5$)(CH$_3$)CH—NH—CO—NH) | 2,660 | >570,000[g] | 440 | 21%[j] |
| 7-(Naphthyl-NH—CO—NH) | 76 | 390,000[g] | 80 | 22%[j] |
| 7-((CH$_3$)$_3$C—CH$_2$—CO—NH) | 3,650 | | 1,070 | 240 |
| 7-(Ph—CH$_2$CO—NH) | 4,950 | 480,000[g] | 82,000[g] | 70 |
| 7-(Boc-D-Phe—NH) | 30 | | 150 | 19%[j] |
| 7-(Boc-L-Phe—NH) | 50 | | 400 | 19%[j] |
| 7-(Boc—Ala—Ala—NH) | 1,670 | 230,000[g] | 2,750[h] 810[h] | 46 |
| 7-(PhNHCSNH) | 1,250 | >480,000[g] | 39,000[g] | 200 |
| 7-(m-COOH—PhNHCSNH) | | >240,000[g] | 1,960 | 320 |
| 7-(p-COOH—PhNHCSNH) | | >390,000[g] | 1,720 | 450 |
| (II). 7-substituted-4-chloro-3-(3-bromopropoxy)isocoumarin | | | | |
| 7-NH$_2$ | 10 | 4,000 | 790 | 210 |
| 7-NO$_2$ | | | | |
| 7-(Ph—NH—CO—NH) | 4 | 13,750[h] 2,890[h] | 180 | 17%[j] |
| 7-(Ph—CH$_2$—NH—CO—NH) | 13 | 15,650 | 440 | 21%[j] |
| 7-(CH$_3$—CO—NH) | 24 | 24,400 | 3,980 | 170 |
| 7-(Ph—CH$_2$—CO—NH) | 28 | 32,350 | 140,000[g] | 28%[j] |
| 7-(Ph—CH$_2$—CH$_2$CO—NH) | | 35,650[h] 9,870[h] | 600 | NI |
| 7-(Boc-D-Phe—NH) | | 1,480 | 70 | NI |
| 7-(Boc-L-Phe—NH) | | 1,320 | 490 | NI |
| (III). 7-substituted-4-chloro-3-(2-bromoisopropoxy)isocoumarin | | | | |
| 7-NO$_2$ | 1,060 | | 200,000[g] | 1,660 |
| 7-NH$_2$ | 62 | 24,000 | 320 | 150 |
| (IV). 7-amino-4-chloro-3-alkoxyisocoumarin | | | | |
| 3-CH$_3$CH$_2$CH$_2$O | 4.3 | 390 | 375 | 61 |

TABLE XVI-continued

Inhibition Rates of Serine Proteases by 7-substituted-4-chloro-3-bromoalkoxyisocoumarins and 7-amino-4-chloro-3-alkoxyisocoumarins[a].

| Compounds | $k_{obs}/[I]$ $(M^{-1}s^{-1})$ | | | |
|---|---|---|---|---|
| | PPE[b] | HLE[c] | Chymotrypsin[d] | Cathepsin G[e] |
| 3-CH$_3$CH$_2$CH$_2$OCH$_2$CH$_2$O | 0.5 | 33 | 140 | 2.6 |

[a]Inhibition rates were measured in 0.1M Hepes, 0.5M NaCl, pH 7.5 buffer, 8-9% Me$_2$SO and at 25° C. Substrates were Suc—Ala—Ala—Ala—NA (0.48 mM) for PPE; MeO—Suc—Ala—Ala—Pro—Val—NA (0.24 mM) for HLE; Suc—Val—Pro—Phe—NA (0.48 mM) for chymotrypsin and cathepsin G.
[b]Inhibitor concentrations were 0.04-2.0 mM.
[c]Inhibitor concentrations were 0.07-710 μM.
[d]Inhibitor concentrations were 1.7-58 μM.
[e]Inhibitor concentrations were 35-710 μM.
[f]Progress curve method was used according to Tian & Tsou (1982) Biochemistry 21, 1028-1032.
[g]Second order rate constant was obtained using equimolar concentration of inhibitor and enzyme.
[h]Biphasic plot was obtained, and two inhibition rates were shown.
[i]NI = No inhibition.
[j]Percentage of inhibition was obtained after 5 min incubation of inhibitor with enzyme.

TABLE XVII

Half-Lives for Deacylation of Elastases Inactivated by 7-Substituted-4-chloro-3-methoxyisocoumarins[a].

| Compounds 7-Substituted | $t_{\frac{1}{2}}$ (h) | |
|---|---|---|
| | HLE | PPE |
| HOOCCH$_2$CH$_2$CONH | 1.5 | 1.3 |
| HOOCCH$_2$CH$_2$CH$_2$CONH | 1.7 | 1.5 |
| o-HOOCC$_6$H$_4$CONH | 5.0 | 17 |
| CH$_3$OOCCH$_2$CH$_2$CH$_2$CONH | 1.0 | 1.0 |
| PhNHCONH | >48 | >48 |

[a]Enzyme activity was followed after removal of excess inhibitors by centrifugation using Amicon centricon-10 microconcentrator.

TABLE XVIII

Half-Lives for Spontaneous Hydrolysis of Isocoumarin Derivatives in Hepes Buffer[a], Human Plasma and Rabbit Plasma.

| Compounds | $t_{\frac{1}{2}}$ (min) | | |
|---|---|---|---|
| | Hepes Buffer | Human Plasma | Rabbit Plasma |
| 3-(3-aminopropoxy)isocoumarin | 606 | | |
| 3-(3-aminopropoxy)-4-chloroisocoumarin | 123 | | |
| 3-(2-isothiureidoethoxy)-4-chloro isocoumarin | 83 | | |
| 3-(3-isothiureidopropoxy)-4-chloro-isocoumarin | 99 | 0.5 | |
| 7-amino-3-(3-isothiureidopropoxy)-4-chloroisocoumarin | 90 | 165 | 140 |
| 7-guanidino-3-methoxyisocoumarin | 252 | | |
| 7-guanidino-3-methoxy-4-chloroisocoumarin | 44 | 6.7 | |
| 7-guanidino-3-ethoxyisocoumarin | 136 | | |
| 7-guanidino-3-ethoxy-4-chloroisocoumarin | 39 | 8.2 | 4.2 |
| 7-guanidino-3-(2-phenylethoxy)-isocoumarin | 140 | | |
| 7-guanidino-3-(2-phenylethoxy)-4-chloro-isocoumarin isocoumarin | 36 | 4.5 | |
| PhCH$_2$NHCONH-CiTPrOIC | 148 | | |
| PhNHCONH-CiTPrOIC | 148 | | |
| CH$_3$CONH-CiTPrOIC | 68 | | |
| PhCH$_2$CH$_2$CONH-CiTPrOIC | 66 | | |
| PhCH$_2$CONH-CiTPrOIC | 61 | | |
| PhNHCONH-CiTEtOIC | 108 | | |

[a]Conditions were 0.1 Hepes, 0.5M NaCl, pH 7.5 and 9% Me$_2$SO at 25° C. Spontaneous hydrolysis rates were measured spectrophotometrically by monitoring the decrease in absorbance due to the isocoumarin ring system (wavelength 335-380 nm) using the first-order rate law.

TABLE XIX

Effect of Substituted Isocoumarins on PT and APTT of Human, Rabbit and Pig Plasma.

| Compounds | [I] (μM) | Human Plasma | | Rabbit Plasma | | Pig Plasma | |
|---|---|---|---|---|---|---|---|
| | | PT (sec) | APTT (sec) | PT (sec) | APTT (sec) | PT (sec) | APTT (sec) |
| Control | 0 | 12.6 | 26.7 | 12.3[a] | 19.0 | 18.6 | 17.7 |
| 3,4-dichloroisocoumarin | 33 | 12.4 | 26.6 | 14.3[b] | | | |
| | 45 | | 26.0 | | | | |
| 7-guanidino-3-methoxy-4-chloro-isocoumarin | 21 | 16.5 | 83.8 | | | | |
| 7-guanidino-3-ethoxy-4-chloro-isocoumarin | 4.3 | | 74.8 | | | | |
| | 15 | | | 14.2[a] | | | |
| | 21 | 22.4 | >120 | | | | |
| | 31 | | | 27.4[a] | 60.5 | | |
| | | | | 17.2[b] | | | |
| | 53 | 31.4 | >120 | | | | |
| | 75 | 44.2 | | | | | |
| | 107 | 80 | >120 | | | | |
| | 124 | | | >120[b] | | | |
| 7-guanidino-3-(2-phenylethoxy)-4-chloroisocoumarin | 27 | 13.0 | 57.3 | | | | |
| 3-(3-isothiureidopropoxy)-4-chloro-isocoumarin | 31 | 12.3 | 25.8 | | | | |
| 7-amino-3-(3-isothiureidopropoxy)-4-chloro-isocoumarin | 2.9 | | 100.8 | | | | |
| | 29 | 19.4 | >120 | | | | |
| | 33 | | | 13.7[a] | 68.6 | | |
| | 131 | | | 62.0[a] | | | |

TABLE XIX-continued

Effect of Substituted Isocoumarins on PT and APTT of Human, Rabbit and Pig Plasma.

| Compounds | [I] (μM) | Human Plasma PT (sec) | Human Plasma APTT (sec) | Rabbit Plasma PT (sec) | Rabbit Plasma APTT (sec) | Pig Plasma PT (sec) | Pig Plasma APTT (sec) |
|---|---|---|---|---|---|---|---|
| PhNHCONH-CiTEtOIC | 16 | | | | | 28.5 | >120 |
| | 32 | | | | | 58.3 | |
| PhCH$_2$NHCONH-CiTEtOIC | 32 | | | | | 31.1 | >120 |
| S-C$_6$H$_5$(CH$_3$)CHNHCONH CiTEtOIC | 32 | | | | | 30.0 | >120 |
| R-C$_6$H$_5$(CH$_3$)CHNHCONH-CitEtOIC | 32 | | | | | 26.2 | >120 |

$^a$Plasma and inhibitor were incubated at 37° C. for 1 min., Dade thromboplastin reagent was then added.
$^b$Plasma and inhibitor were incubated at 37° C. for 3 min., Orthobrain thromboplastin reagent was then added.

What is claimed is:

1. A process for the inhibition of the enzymatic activity of serine proteases comprising the step of adding to a medium containing the protease that amount of inhibitor effective to inhibit said activity having the following structure:

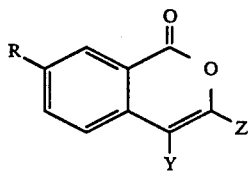

or a pharmaceutically acceptable salt thereof, wherein R is selected from the group consisting of M—NH—, M—O—, AA—NH—, AA—AA—NH—, AA—O—, AA—AA—O—, M—AA—NH—, M—AA—AA—NH—, M—AA—O—, M—AA—AA—O—, wherein M represents NH$_2$—CO—, NH$_2$—CS—, NH$_2$—SO$_2$—, X—NH—CO—, X—NH—CS—, X—NH—SO$_2$—, X—CO—, X—CS—, X—SO$_2$—, X—O—CO—, or X—O—CS—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, wherein X represents C$_{1-6}$ alkyl, C$_{1-6}$ fluoroalkyl, C$_{1-6}$ alkyl substituted with K, C$_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, C$_{1-6}$ alkyl with an attached phenyl group, C$_{1-6}$ alkyl with two attached phenyl groups, C$_{1-6}$ alkyl with an attached phenyl group substituted with J, or C$_{1-6}$ alkyl with two attached phenyl groups substituted with J, wherein J represents halogen, COOH, OH, CN, NO$_2$, NH$_2$, C$_{1-6}$ alkyl, C$_{1-6}$ alkoxy, C$_{1-6}$ alkylamine, C$_{1-6}$ dialkylamine, C$_{1-6}$ alkyl—O—CO—, or C$_{1-6}$ alkyl—O—CO—NH—, wherein K represents halogen, COOH, OH, CN, NO$_2$, NH$_2$, C$_{1-6}$ alkoxy, C$_{1-6}$ alkylamine, C$_{1-6}$ dialkylamine, C$_{1-6}$ alkyl—O—CO—, or C$_{1-6}$ alkyl—O—CO—NH—, Z is selected from the group consisting of C$_{1-6}$ alkoxy with an amino group attached to the alkoxy group, C$_{1-6}$ alkoxy with an isothiureido group attached to the alkoxy group, C$_{1-6}$ alkoxy with a guanidino group attached to the alkoxy group, C$_{1-6}$ alkoxy with an amidino group attached to the alkoxy group, C$_{1-6}$ alkyl with an amino group attached to the alkyl group, C$_{1-6}$ alkyl with an isothiureido group attached to the alkyl group, C$_{1-6}$ alkyl with a guanidino group attached to the alkyl group, C$_{1-6}$ alkyl with an amidino group attached to the alkyl group, Y is selected from the group consisting of H, halogen, trifluoromethyl, methyl, OH, and methoxy.

2. A process for the inhibition of the enzymatic activity of serine proteases comprising the step of adding to a medium containing the protease that amount of inhibitor effective to inhibit said activity having the following structure:

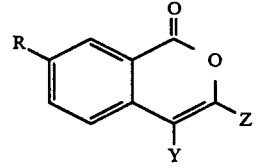

or a pharmaceutically acceptable salt thereof, wherein —R is selected from the group consisting of M—O—, M—AA—AA—NH—, M—AA—O—, M—AA—AA—O, wherein M represents NH$_2$—CO—, NH$_2$—CS—, NH$_2$—SO$_2$—, X—NH—CO—, X—NH—CS—, X—NH—SO$_2$—, X—CS—, X—O—CO—, X—O—CS—, benzoyl with a J substituent attached to the benzoyl group, phenylsulfonyl with a J substituent attached to the phenylsulfonyl group, C$_{1-6}$ alkylsulfonyl with a K substituent attached to the C$_{1-6}$ alkylsulfonyl group, C$_{2-6}$ alkanoyl with a phenyl group attached to the C$_{2-6}$ alkanoyl group, or C$_{2-6}$ alkanoyl with a phenyl group substituted with J attached to the C$_{2-6}$ alkanoyl group, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, Z is selected from the group consisting of $C_{1-6}$ alkyl, $C_{1-6}$ alkoxy, $C_{1-6}$ alkyl with a phenyl group attached to the $C_{1-6}$ alkyl, $C_{1-6}$ alkoxy with a phenyl group attached to the $C_{1-6}$ alkoxy, Y is selected from the group consisting of H, halogen, trifluoromethyl, methyl, OH, and methoxy.

3. A process for the inhibition of the enzymatic activity of serine proteases comprising the step of adding to a medium containing the protease that amount of inhibitor effective to inhibit said activity having the following structure:

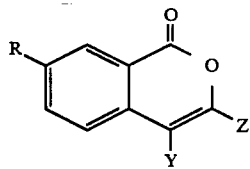

or a pharmaceutically acceptable salt thereof, wherein
R is selected from the group consisting of M—NH—, M—O—, AA—NH—, AA—AA—NH—, AA—O—, AA—AA—O—, M—AA—NH—, M—AA—AA—NH—, M—AA—O—, M—AA—AA—O—, wherein M represents $NH_2$—CO—, $NH_2$—CS—, $NH_2$—$SO_2$—, X—NH—CO—, X—NH—CS—, X—NH—$SO_2$—, X—CO—, X—CS—, X—$SO_2$—, X—O—CO—, or X—O—CS—, wherein AA represents alanine, valine, leucine, isoleucine, proline, methionine, phenylalanine, tryptophan, glycine, serine, threonine, cysteine, tyrosine, asparagine, glutamine, aspartic acid, glutamic acid, lysine, arginine, histidine, beta-alanine, norleucine, norvaline, phenylglycine, alpha-aminobutyric acid, epsilon-aminocaproic acid, citrulline, hydroxyproline, ornithine or sarcosine, wherein X represents $C_{1-6}$ alkyl, $C_{1-6}$ fluoroalkyl, $C_{1-6}$ alkyl substituted with K, $C_{1-6}$ fluoroalkyl substituted with K, phenyl, phenyl substituted with J, phenyl disubstituted with J, phenyl trisubstituted with J, naphthyl, naphthyl substituted with J, naphthyl disubstituted with J, naphthyl trisubstituted with J, $C_{1-6}$ alkyl with an attached phenyl group, $C_{1-6}$ alkyl with two attached phenyl groups, $C_{1-6}$ alkyl with an attached phenyl group substituted with J, or $C_{1-6}$ alkyl with two attached phenyl groups substituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, or $C_{1-6}$ alkyl-O—CO—NH—, Z is selected from the group consisting of $C_{1-6}$ alkoxy with a bromine attached to the alkoxy group, $C_{1-6}$ alkyl with a bromine attached to the alkyl group, $C_{1-6}$ alkoxy with an attached $C_{1-6}$ alkoxy group substituted with Q, wherein Q represents H, or $C_{1-6}$ alkoxy, Y is selected from the group consisting of H, halogen, trifluoromethyl, methyl, OH, and methoxy.

4. A process for the inhibition of the enzymatic activity of serine proteases comprising the step of adding to a medium containing the protease that amount of inhibitor effective to inhibit said activity having the following structure:

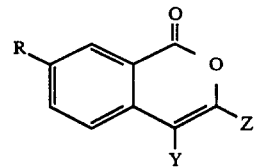

or a pharmaceutically acceptable salt thereof, wherein
R is $C_{1-6}$ alkyl with an isothiureido group of the formula —S—C(=NH)$NH_2$ attached to the alkyl group, Z is selected from the group consisting of H, halogen, $C_{1-6}$ alkyl, $C_{1-6}$ fluorinated alkyl, $C_{1-6}$ alkyl substituted with K, $C_{1-6}$ fluorinated alkyl substituted with K, $C_{1-6}$ alkoxy, $C_{1-6}$ fluorinated alkoxy, $C_{1-6}$ alkoxy substituted with K, $C_{1-6}$ fluorinated alkoxy substituted with K, $C_{1-6}$ alkyl with a phenyl group attached to the alkyl group, $C_{1-6}$ alkoxy with a phenyl group attached to the alkoxy group, $C_{1-6}$ alkyl with an attached phenyl group substituted with J, $C_{1-6}$ alkyl with an attached phenyl group disubstituted with J, $C_{1-6}$ alkoxy with an attached phenyl group substituted with J, $C_{1-6}$ alkoxy with an attached phenyl group disubstituted with J, wherein J represents halogen, COOH, OH, CN, $NO_2$, $NH_2$, $C_{1-6}$ alkyl, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, or $C_{1-6}$ alkyl-S—, wherein K represents halogen, COOH, OH, CN, $NO_2$, $NH_2$, $C_{1-6}$ alkoxy, $C_{1-6}$ alkylamine, $C_{1-6}$ dialkylamine, $C_{1-6}$ alkyl-O—CO—, $C_{1-6}$ alkyl-O—CO—NH—, $C_{1-6}$ alkyl-S—, or tosylamino, Y is selected from the group consisting of H, halogen, trifluoromethyl, methyl, OH, and methoxy.

5. A process for the inhibition of the enzymatic activity of serine proteases comprising the step of adding to a medium containing the protease that amount of inhibitor effective to inhibit said activity having the following structure:

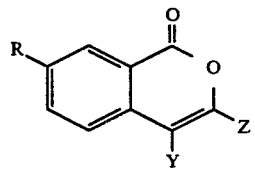

or a pharmaceutically acceptable salt thereof, wherein R is selected from the group consisting of —NH—C(=NH)NH$_2$, —C(=NH)NH$_2$, C$_{1-6}$ alkyl with an amino group attached to the C$_{1-6}$ alkyl, C$_{1-6}$ alkyl with an isothiureido group attached to the C$_{1-6}$ alkyl, Z is selected from the group consisting of C$_{1-6}$ alkoxy with an amino group attached to the alkoxy group, C$_{1-6}$ alkoxy with an isothiureido group attached to the alkoxy group, C$_{1-6}$ alkoxy with a guanidino group attached to the alkoxy group, C$_{1-6}$ alkoxy with an amidino group attached to the alkoxy group, C$_{1-6}$ alkyl with an amino group attached to the alkyl group, C$_{1-6}$ alkyl with an isothiureido group attached to the alkyl group, C$_{1-6}$ alkyl with a guanidino group attached to the alkyl group, C$_{1-6}$ alkyl with an amidino group attached to the alkyl group, Y is selected from the group consisting of H, halogen, trifluoromethyl, methyl, OH, and methoxy.

* * * * *